United States Patent [19]

Bowers et al.

[11] Patent Number: 4,880,778

[45] Date of Patent: Nov. 14, 1989

[54] COMBINATIONS HAVING SYNERGISTIC GROWTH HORMONE RELEASING ACTIVITY AND METHODS FOR USE THEREOF

[75] Inventors: Cyril Y. Bowers, New Orleans, La.; Frank A. Momany, Concord, Mass.; Ching H. Chang; Wayne Cody, both of Kingsport, Tenn.; John C. Hubbs, Gray; Charles H. Foster, Kingsport, both of Tenn.

[73] Assignee: Eastman Kodak Company, Rochester, N.Y.

[21] Appl. No.: 37,275

[22] Filed: Apr. 10, 1987

Related U.S. Application Data

[63] Continuation-in-part of Ser. No. 861,968, May 12, 1986, abandoned.

[51] Int. Cl.$^4$ ............................................. H61K 37/43
[52] U.S. Cl. ............................................................ 514/12
[58] Field of Search ............................................. 514/12

[56] References Cited

U.S. PATENT DOCUMENTS

| | | | |
|---|---|---|---|
| 4,061,626 | 12/1977 | Shields | 260/112.5 |
| 4,105,603 | 8/1978 | Vale, Jr. et al. | 260/8 |
| 4,127,517 | 11/1978 | Coy et al. | 260/8 |
| 4,127,518 | 11/1978 | Coy et al. | 260/8 |
| 4,127,519 | 11/1978 | Coy et al. | 260/8 |
| 4,127,520 | 11/1978 | Coy et al. | 260/8 |
| 4,127,521 | 11/1978 | Coy et al. | 260/8 |
| 4,127,522 | 11/1978 | Coy et al. | 260/8 |
| 4,127,523 | 11/1978 | Coy et al. | 260/8 |
| 4,127,524 | 11/1978 | Coy et al. | 260/8 |
| 4,127,525 | 11/1978 | Coy et al. | 260/8 |
| 4,127,526 | 11/1978 | Coy et al. | 260/8 |
| 4,127,527 | 11/1978 | Coy et al. | 260/8 |
| 4,127,528 | 11/1978 | Coy et al. | 260/8 |
| 4,127,529 | 11/1978 | Coy et al. | 260/8 |
| 4,127,530 | 11/1978 | Coy et al. | 260/8 |
| 4,127,531 | 11/1978 | Coy et al. | 260/8 |
| 4,127,532 | 11/1978 | Coy et al. | 260/8 |
| 4,127,533 | 11/1978 | Coy et al. | 260/8 |
| 4,127,534 | 11/1978 | Coy et al. | 260/8 |
| 4,127,535 | 11/1978 | Coy et al. | 260/8 |
| 4,127,536 | 11/1978 | Coy et al. | 260/8 |
| 4,127,537 | 11/1978 | Coy et al. | 260/8 |
| 4,127,538 | 11/1978 | Coy et al. | 260/8 |
| 4,127,539 | 11/1978 | Coy et al. | 260/8 |
| 4,127,540 | 11/1978 | Coy et al. | 260/8 |
| 4,127,541 | 11/1978 | Coy et al. | 260/8 |
| 4,139,504 | 2/1979 | Coy et al. | 260/8 |
| 4,178,284 | 12/1979 | Sarantakis | 260/112.5 |
| 4,211,693 | 7/1980 | Rivier et al. | 260/112.5 |
| 4,223,019 | 9/1980 | Momany | 424/177 |
| 4,223,020 | 9/1980 | Momany | 424/177 |
| 4,223,021 | 9/1980 | Momany | 424/177 |
| 4,224,316 | 9/1980 | Momany | 424/177 |
| 4,226,857 | 10/1980 | Momany | 424/177 |
| 4,228,155 | 10/1980 | Momany | 424/177 |
| 4,228,156 | 10/1980 | Momany | 424/177 |
| 4,228,157 | 10/1980 | Momany | 424/177 |
| 4,228,158 | 10/1980 | Momany | 424/177 |
| 4,312,857 | 1/1982 | Coy et al. | 424/177 |
| 4,316,891 | 2/1982 | Guillemin et al. | 424/177 |
| 4,350,627 | 9/1982 | de Castiglione et al. | 260/112.5 |
| 4,372,884 | 2/1983 | Brown et al. | 260/112.5 |
| 4,393,050 | 7/1983 | Vale, Jr. et al. | 424/177 |
| 4,410,512 | 10/1983 | Bowers | 424/177 |
| 4,410,513 | 10/1983 | Momany | 424/177 |
| 4,411,890 | 10/1983 | Momany | 424/177 |
| 4,428,942 | 1/1984 | Rivier et al. | 424/177 |
| 4,491,541 | 1/1985 | de Castiaglione et al. | 260/112.5 |
| 4,505,897 | 3/1985 | Coy et al. | 514/11 |
| 4,508,711 | 4/1985 | Coy et al. | 514/11 |
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1976 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | DiMarchi et al. | 530/324 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,131 | 3/1987 | Felix et al. | 514/12 |

OTHER PUBLICATIONS

P. K. Baker et al., J. Animal Science 59 (Supplement 1), 220 (1984).
W. J. Croom et al., J. Dairy Sci. 67 (Supplement 1), 109 (1984).
S. N. McCutcheon et al., J. Dairy Sci. 67, 2881 (1984).
P. Brazeau et al., Proc. Natl. Acad. Sci. 79, 7909 (1982).
M. O. Thorner et al., Lancet 1,24 (1983).
C. Y. Bowers et al., Endocrinology 114, 1537 (1984).
F. A. Momany et al., Endocrinology 114, 1531 (1984).
C. Y. Bowers, 7th International Congress of Endocrinology Ab., 464 (1984).
W. B. Wehrenberg et al., Endocrinology 115, 1218 (1984).
C. Rivier et al., Endocrinology 100, 238 (1977).
C. Y. Bowers, Endocrinology 117, 1441 (1985).
E. L. Lien et al., FEBS Letters 88, 208 (1978).

*Primary Examiner*—Delbert R. Phillips
*Attorney, Agent, or Firm*—S. E. Reiter; William P. Heath, Jr.

[57] ABSTRACT

Disclosed are combinations of polypeptides acting in a synergistic manner to promote release and elevation of growth hormone levels in the blood of animals. Also disclosed are methods of promoting the release and elevation of growth hormone levels in the blood of animals using the disclosed combination of polypeptides.

32 Claims, No Drawings

COMBINATIONS HAVING SYNERGISTIC GROWTH HORMONE RELEASING ACTIVITY AND METHODS FOR USE THEREOF

This application is a continuation-in-part of copending S.N. 861,968, filed May 12, 1986, now abandoned.

1. Field of Invention

The invention herein described relates to novel methods to promote release, and to produce elevated growth hormone (GH) levels in the blood of animals; and to combinations of polypeptide compounds acting in a synergistic manner to promote release and to produce elevated growth hormone (GH) levels in the blood of animals.

2. Description of the Art

It has been established in the scientific literature that the elevation of growth hormone levels in mammals upon administration of GH-releasing compounds can lead to enhanced body weight and to enhanced milk production if sufficiently elevated GH levels occur upon administration (c.f., P. K. Baker, et al., *J. Animal Science* 59 (supplement 1), 220 (1984); W. J. Croom et al., *J. Dairy Sci.* 67 (supplement 1), 109 (1984); S. N. McCutcheon et al., *J. Dairy Sci.* 67, 2881 (1984)). Further, it is known that the elevation of growth hormone levels in mammals can be accomplished by application of known growth hormone releasing agents, such as endogenous growth hormone releasing hormones (GHRH's, #144–#149) included herein as members of the group designated as "Group 1 compounds" (c.f., P. Brazeau et al., *Proc. Natl. Acad. Sci.* 79, 7909 (1982), and M. O. Thorner et al., *Lancet* 1,24 (1983)). The elevation of growth hormone levels in mammals can also be accomplished by application of growth hormone releasing peptides (GRP's), some of which have been previously described and are included herein as members of the group designated as "Group 2 compounds" (c.f. C. Y. Bowers et al., *Endocrinology* 114, 1537 (1984), F. A. Momany et al., *Endocrinology* 114, 1531 (1984) and C. Y. Bowers, *7th International Congress of Endocrinology Abstracts*, 464 (1984)). Antibodies to the endogenous growth hormone release inhibitor, somatostatin (SRIF) are also used to elevate GH levels. In the last case, growth hormone levels are elevated by removing the endogenous GH-release inhibitor (SRIF) before it reaches the pituitary, where it inhibits the release of GH (c.f. W. B. Wehrenberg et al., *Endocrinology* 115, 1218 (1984)). Finally, it has been shown that some compounds such as morphine (c.f. C. Rivier et al., *Endocrinology* 100, 238 (1977)) and other alkaloids (c.f. C. Y. Bowers, *Endocrinology* 117, 1441 (1985)) and DAla$^2$, DLeu$^5$-enkephalinamide (c.f. E. L. Lien et al., *FEBS Letters* 88, 208 (1978)) also release growth hormone by acting on the hypothalamus. The Group 3 compounds described herein may also act at the hypothalamus.

SUMMARY

It is an object of this invention to provide novel combinations of growth hormone releasing compounds which directly or indirectly produce elevated levels of growth hormone in the blood of animals. Such combinations of compounds have enhanced stabilities, solubilities, physiochemical properties and biological activities relative to growth hormone releasing compounds of the prior art.

It is another object of this invention to provide, by administration of a combination of active ingredients described in greater detail below, a method for elevating GH levels in animals for use in the pharmaceutical and animal products industries.

Yet another object of this invention is to provide a variety of each of three differently acting growth hormone releasing compounds, each of which can be combined in different ways and as part of different compositions, to allow optimization in the design of formulas for different utilities, such as in the enhancement of growth; and the improvement in milk, fur or wool production.

Each of the groups of agents referred to above and their analogs act to promote the release of growth hormone in animals through different mechanisms, thus, the synergistic effect of the combination of compounds described herein in elevating the GH levels in vivo is unusual and unexpected for the combination of compounds between groups, as described herein. Further, the magnitude of the synergistic GH response to an effective dose of the combination of compounds between groups is not found in any single compound within a group, at similar doses.

How the compounds described in this invention act to achieve their remarkable synergistic effect is not fully understood at the molecular level. Clearly one might expect to see additive effects from application of combinations of these compounds. However, the very important synergistic results and their utility will become apparent in light of the accompanying disclosure. Of novelty to this preparation is the discovery by the authors that the Group 1 compounds described herein act synergistically with Group 2 compounds, to promote the release of much more GH than equivalent amounts of the individual compounds within groups, when given alone. In addition, the authors have discovered that the Group 1 compounds described herein act synergistically with Group 3 compounds, to promote the release of much more GH than equivalent amounts of the individual compounds within groups, when given alone. The authors have also discovered that the Group 2 compounds described herein act synergistically with Group 3 compounds, to promote the release of much more GH than equivalent amounts of the individual components within groups, when given alone. Further, the authors have recently shown that specific Group 3 compounds, such as the naturally occurring dermorphins, hereinafter referred to as compounds #8801 and #8802, also act synergistically with both Group 1 and 2 compounds, such that a combination mixture of all three groups of compounds is a potent GH-releasing mixture.

The present invention provides combinations having synergistic GH-releasing effects. The combinations of this invention may be used to enhance blood GH levels in animals; enhance milk production in cows; enhance body growth in animals such as mammals (e.g., humans, sheep, bovines, and swine), as well as fish, fowl and crustaceans; and increase wool and/or fur production in mammals. The amount of body growth is dependent upon the sex and age of the animal species, quantity and identity of the growth hormone releasing compound being administered, and route of administration.

DETAILED DESCRIPTION OF THE INVENTION

This invention is concerned with novel combinations of polypeptides acting in a synergistic manner to promote, the release of and thereby produce elevated growth hormone levels in the blood of animals. The invention is also concerned with methods for use of the novel composition.

In its broadest scope, the present invention provides a combination effective to cause the release and elevation of the level of growth hormone in the blood of an animal, the combination comprising an effective amount of polypeptides selected from at least two different groups of the Group 1 polypeptides, Group 2 polypeptides or Group 3 polypeptides hereinafter described in greater detail.

In accordance with this broadest scope of the present invention, the term "Group 1 polypeptides" is intended to include naturally occurring growth hormone releasing hormones, e.g., human, porcine, bovine, ovine and rat growth hormone releasing hormones, such as compounds #144-149 below, and functional analogs thereof. Such peptides act at the growth hormone releasing hormone receptor of mammals and other vertebrates, crustaceans and the like, to cause the release of growth hormone. Representative peptides included within this definition are selected from any of the polypeptides:

(a) having the following amino acid sequences in positions 1-44 (numbered from N terminus to C terminus):
(#144)  YADAIFTNSYRKVLGQLSARKLL-QDIMSRQQGESNQERGARARL-X,
(#145)  YADAIFTNSYRKVLGQLSARKLL-QDIMSRQQGERNQEQGARVRL-X,
(#146)  YADAIFTNSYRKVLGQLSARKLL-QDIMNRQQGERNQEQGAKVRL-X,
(#148)  YADAIFTNSYRKILGQLSARKLL-QDIMNRQQGERNQEQGAKVRL-X, and
(#149)  HADAIFTSSYRRILGQLYARKL-LHEIMNRQQGERNQEQRSRFN-X;
wherein the C-terminal amino acid has the following truncated general formula:

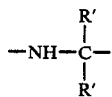

wherein each R' independently represents the substituents of the particular amino acid residue, e.g.; hydrogen, alkyl, aryl, amino or acid substituents; X denotes the C terminal end group and is selected from —CONH$_2$, —COOH, —COOR, —CONRR, —CH$_2$OH, and —CH$_2$OR, where R is an alkyl group having 1-6 carbon atoms or an aromatic ring having up to 12 carbon atoms; and wherein the amino acid residue abbreviations used are in accordance with the standard peptide nomenclature:
G=Gly (Glycine)
Y=Tyr (L-Tyrosine)
I=Ile (L-Isoleucine)
E=Glu (L-Glutamic Acid)
T=Thr (L-Threonine)
F=Phe (L-Phenylalanine)
A=Ala (L-Alanine)
K=Lys (L-Lysine)
D=Asp (L-Aspartic Acid)
C=Cys (L-Cysteine)
R=Arg (L-Arginine)
Q=Gln (L-Glutamine)
P=Pro (L-Proline)
L=Leu (L-Leucine)
M=Met (L-Methionine)
S=Ser (L-Serine)
N=Asn (L-Asparagine)
H=His (L-Histidine)
W=Trp (L-Tryptophan)
V=Val (L-Valine)
wherein all three letter amino acid abbreviations preceded by a "D" indicate the D-configuration of the amino acid residue.

While essentially stereochemically pure D or L amino acids are referred to throughout this specification, it is to be understood that mixtures of the D/L stereoisomers of the amino acid residues are also operable, while sometimes having a reduced level of biological activity as a function of the relative amount of the unspecified configuration which is present. Additional amino acid and peptide abbreviations which appear throughout the specification include:
Abu: alpha-Aminobutyric Acid
Aib: alpha-Aminoisobutyric acid
Arg(NO$_2$): Ng-Nitro-L-Arginine
(beta)Ala: beta-Alanine (i.e., 3-Amino Propanoic Acid)
Dab: 2,4-Diaminobutyric Acid
DOPA: 3,4-Dihydroxyphenylalanine
Gly-ol: 2-Aminoethanol
Hyp: trans-4-Hydroxy-L-Proline
Met(O): Methionine sulfoxide
Met(O)-ol: Methionine sulfoxide alcohol
Nle: L-Norleucine
Pal: 3-Pyridyl Alanine
Pgl: Phenylglycine
Sar: Sarcosine
Sar-ol: Sarcosine alcohol
Thz: L-Thiazolidine-4-carboxylic acid Either:
The Dermorphins: Tyr-DAla-Phe-Gly-Tyr-Pro-Ser-NH$_2$ (#8801) or Tyr-DAla-Phe-Gly-Tyr-Hyp-Ser-NH$_2$ (#8802)

(b) any one of said (a) polypeptides having the following amino acid substitutions:
position 1 of (#144–#148) is DTyr or His;
position 1 of (#149) is Tyr or DHis;
position 2 of (#144–#149) is (NMe)DAla or Aib or DAla;
position 3 of (#144–#149) is DAsp;
position 4 of (#144–#149) is DAla; and
position 1+2 of (#144–#149) is;
DTyr$^1$+DAla$^2$, DTyr$^1$+(NMe)DAla$^2$, or DTyr$^1$+Aib$^2$;

(c) any one of said (a) or (b) polypeptides having a substitution of Nle for Met at position 27;

(d) any one of said (a), (b) or (c) polypeptides in which the N-terminus —NH$_2$ is replaced by —NHCOR and wherein R is an alkyl group having 1 to 6 carbon atoms, or an aromatic ring having up to 12 carbon atoms;

(e) fragments of any one of said (a), (b), (c) or (d) polypeptides which contain at least the amino acid residues of positions 1-29;

(f) having the following specific amino acid sequences in positions 1-29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and YADAIFTNCYRKVLCQLSARKLLQDIMSR-X (cyclic disulfide);
wherein the C-terminal amino acid and X are as defined above; and modification of any one of these group (f) compounds in accordance with the modifications set forth in (b), (c) and (d) above; and (g) organic or inorganic addition salts of any of said (a), (b), (c), (d), (e) or (f) polypeptides of Group 1.

Group 2 polypeptides contemplated within the broad scope of the present invention are selected from any of the polypeptides having the structure:
Ala-His-DTrp-Ala-Trp-DPhe-Lys-Gly-Tyr-NH₂;
Ala-His-(formyl)DTrp-Ala-Trp-DPhe-Lys-NH₂ (DTrp is formylated at the indole nitrogen);
Ala-His-DTrp-Ser-Trp-DPhe-Lys-NH₂;
Cys-Ala-His-DTrp-Ala-Trp-DPhe-Lys-Cys-NH₂ (cyclic disulfide);
Cys-Ala-His-DTrp-Ala-Trp-DPhe-Lys-Cys-NH₂ (free dithiol);
DOPA-Ala-His-DTrp-Ala-Trp-DPhe-Lys-NH₂;
His-DTrp-Ala-Trp-DPhe-Lys-NH₂;
His-DTrp-Ala-Trp-DPhe-Lys-Ala-Tyr-NH₂;
Lys-Ala-His-DTrp-Ala-Trp-DPhe-Lys-NH₂;
Lys-His-DTrp-Ala-Trp-DPhe-Asp-NH₂;
Phe-Ala-His-DTrp-Ala-Trp-DPhe-Lys-NH₂;
Tyr-Ala-Gly-Thr-Ala-His-DTrp-Ala-Trp-DPhe-Lys-NH₂;
Tyr-Ala-His-DTrp-Ala-Trp-DPhe-Lys-NH₂;
Tyr-DAla-Phe-Gly-Ala-His-DTrp-Ala-Trp-DPhe-Lys-NH₂;
Tyr-DAla-Gly-Phe-Ala-His-DTrp-Ala-Trp-DPhe-Lys-NH₂;
Ala-His-XTrp*-Ala-Trp-DPhe-Lys-NH₂ (*XTrp is selected from the group consisting of all N-monomethylated Trp isomers, i.e., (NᵅMe)Trp, (NᵅMe)DTrp, (indole NMe)Trp and (indole NMe)DTrp);
Z-His-DTrp-Ala-Trp-DPhe-Lys-NH₂;
wherein Z is selected from the group consisting of all naturally occurring L-amino acids, Met(O), DOPA and Abu;
and organic or inorganic addition salts of any of said polypeptides of Group 2; and Group 3 polypeptides contemplated within the broad scope of the present invention are selected from any of the polypeptides having the structure:
Tyr-DArg-Phe-NH₂;
Tyr-DAla-Phe-NH₂;
Tyr-DArg(NO₂)-Phe-NH₂;
Tyr-DMet(O)-Phe-NH₂;
Tyr-DAla-Phe-Gly-NH₂;
Tyr-DArg-Phe-Gly-NH₂;
Tyr-DThr-Phe-Gly-NH₂;
Phe-DArg-Phe-Gly-NH₂;
Tyr-DArg-Phe-Sar;
Tyr-DAla-Gly-Phe-NH₂;
Tyr-DArg-Gly-Trp-NH₂;
Tyr-DArg(NO₂)-Phe-Gly-NH₂;
Tyr-DMet(O)-Phe-Gly-NH₂;
(NMe)Tyr-DArg-Phe-Sar-NH₂;
Tyr-DArg-Phe-Gly-ol;
Tyr-DArg-Gly-(NMe)Phe-NH₂;
Try-DArg-Phe-Sar-ol;
Tyr-DAla-Phe-Sar-ol;
Tyr-DAla-Phe-Gly-Tyr-NH₂;
Gly-Tyr-DArg-Phe-Gly-NH₂;
Tyr-DThr-Gly-Phe-Thz-NH₂;
Gly-Tyr-DAla-Phe-Gly-NH₂;
Tyr-DAla-Phe-Gly-ol;
Tyr-DAla-Gly-(NMe)Phe-Gly-ol;
Tyr-DArg-Phe-Sar-NH₂;
Tyr-DAla-Phe-Sar-NH₂;
Tyr-DAla-Phe-Sar;
Tyr-DAla-Gly-(NMe)Phe-NH₂;
Sar-Tyr-DArg-Phe-Sar-NH₂;
Tyr-DCys-Phe-Gly-DCys-NH₂ (cyclic disulfide);
Tyr-DCys-Phe-Gly-DCys-NH₂ (free dithiol);
Tyr-DCys-Gly-Phe-DCys-NH₂ (cyclic disulfide);
Tyr-DCys-Gly-Phe-DCys-NH₂ (free dithiol);
Tyr-DAla-Phe-Gly-Tyr-Pro-Ser-NH₂;
Tyr-DAla-Phe-Sar-Tyr-Pro-Ser-NH₂;
Tyr-DAla-Phe-Sar-Phe-Pro-Ser-NH₂;
Tyr-DAla-Phe-Gly-Tyr-Hyp-Ser-NH₂;
Tyr-DAla-Phe-Sar-Tyr-Hyp-Ser-NH₂;
Tyr-DAla-Phe-Sar-Phe-Hyp-Ser-NH₂;
Tyr-DArg-Phe-Gly-Tyr-Hyp-Ser-NH₂;
Tyr-DArg-Phe-Sar-Tyr-Pro-Ser-NH₂;
Tyr-DArg-Phe-Sar-Tyr-Hyp-Ser-NH₂;
Tyr-DArg-Phe-Gly-Tyr-Pro-Ser-NH₂; and
organic or inorganic addition salts of any of said polypeptides of Group 3.

In a preferred embodiment, the present invention provides a combination effective to cause the release and elevation of growth hormone in the blood of an animal, the combination comprising an effective amount of polypeptides selected from at least two different groups of the Group 1 polypeptides, Group 2 polypeptides or Group 3 polypeptides set forth below.

In accordance with this preferred embodiment of the present invention, the term "Group 1 polypeptides" is intended to include naturally occurring growth hormones, e.g., human, porcine, bovine, ovine and rat growth hormone releasing hormones, such as compounds #144–149 below, and functional analogs thereof, which polypeptides act at the growth hormone releasing hormone receptor of mammals and other vertebrates. Compounds within this definition are selected from any of the polypeptides:

(a) having the following amino acid sequences in positions 1–44 (numbered from N terminus to C terminus):
(#144)  YADAIFTNSYRKVLGQLSARKLL-QDIMSRQQGESNQERGARARL-CONH₂ (hGHRH),
(#145)  YADAIFTNSYRKVLGQLSARKLL-QDIMSRQQGERNQEQGARVRL-CONH₂ (pGHRH),
(#146)  YADAIFTNSYRKVLGQLSARKLL-QDIMNRQQGERNQEQGAKVRL-CONH₂ (bGHRH),
(#148)  YADAIFTNSYRKILGQLSARKLL-QDIMNRQQGERNQEQGAKVRL-CONH₂ (oGHRH), and
(#149)  HADAIFTSSYRRILGQLYARKL-LHEIMNRQQGERNQEQRSRFN-COOH (rGHRH):
wherein the single letter abbreviation for the amino acid residues are as previously defined including the previous definition for the C-terminal amino acid residues;

(b) any one of said (a) polypeptides having the following amino acid substitutions:
position 1 of (#144–#148) is DTyr or His;
position 1 of (#149) is Tyr;
position 2 of (#144–#149) is (NMe)DAla or Aib or DAla;
position 3 of (#144–#149) is DAsp;
position 4 of (#144–#149) is DAla;

position 1+2 of (#144–#149) is DTyr$^1$+DAla$^2$;

(c) any one of said (a) or (b) polypeptides having a substitution of Nle for Met at position 27;

(d) any one of said (a), (b), or (c) polypeptides in which the N-terminus —NH$_2$ is replaced by —NHCOCH$_3$;

(e) fragments of any one of said (a), (b), (c) or (d) polypeptides which contain at least the amino acid residues of positions 1–29, (f) having the following amino acid sequences in positions 1–29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X (cyclic disulfide);
wherein the C-terminal amino acid and X are as defined above; and modification of any one of these group (f) compounds in accordance with the modifications set forth in (b), (c) and (d) above; and (g) organic or inorganic addition salts of any of said (a), (b), (c), (d), (e) or (f) polypeptides of Group 1.

Group 2 polypeptides contemplated within this preferred scope of the invention are selected from any of the polypeptides having the structure:
His-DTrp-Ala-Trp-DPhe-Lys-NH$_2$;
DOPA-Ala-His-DTrp-Ala-Trp-DPhe-Lys-NH$_2$;
Phe-Ala-His-DTrp-Ala-Trp-DPhe-Lys-NH$_2$;
His-DTrp-Ala-Trp-DPhe-Lys-Ala-Tyr-NH$_2$;
Lys-Ala-His-DTrp-Ala-Trp-DPhe-Lys-NH$_2$;
Tyr-Ala-His-DTrp-Ala-Trp-DPhe-Lys-NH$_2$;
Ala-His-(formyl)DTrp-Ala-Trp-DPhe-Lys-NH$_2$ (DTrp is formylated at the indole nitrogen);
Ala-His-DTrp-Ser-Trp-DPhe-Lys-NH$_2$;
Lys-His-DTrp-Ala-Trp-DPhe-Asp-NH$_2$; and
Z-His-DTrp-Ala-Trp-DPhe-Lys-NH$_2$;
wherein Z is selected from the group consisting of all naturally occurring L-amino acids, Met(O), DOPA and Abu; and
organic or inorganic addition salts of any of said polypeptides of Group 2; and Group 3 polypeptides contemplated within this preferred scope of the invention are selected from any of the polypeptides having the structure:
Tyr-DArg-Phe-NH$_2$;
Tyr-DArg(NO$_2$)-Phe-NH$_2$;
Tyr-DMet(O)-Phe-NH$_2$;
Tyr-DAla-Phe-Gly-NH$_2$;
Tyr-DArg-Phe-Gly-NH$_2$;
Tyr-DArg-Phe-Sar;
Tyr-DAla-Gly-Phe-NH$_2$;
Tyr-DAla-Gly-(NMe)Phe-Gly-ol;
Tyr-DAla-Phe-Sar-NH$_2$;
Tyr-DAla-Phe-Sar-NH$_2$;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Tyr-DAla-Phe-Gly-ol;
Tyr-DAla-Phe-Gly-Tyr-NH$_2$;
Gly-Tyr-DArg-Phe-Gly-NH$_2$;
Gly-Tyr-DAla-Phe-Gly-NH$_2$;
Sar-Tyr-DArg-Phe-Sar-NH$_2$;
Tyr-DCys-Phe-Gly-DCys-NH$_2$ (cyclic disulfide);
Tyr-DCys-Phe-Gly-DCys-NH$_2$ (free dithiol)
Tyr-DCys-Gly-Phe-DCys-NH$_2$ (cyclic disulfide);
Tyr-DCys-Gly-Phe-DCys-NH$_2$ (free dithiol);
Tyr-DAla-Phe-Gly-Tyr-Pro-Ser-NH$_2$;
Tyr-DAla-Phe-Sar-Tyr-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DArg-Phe-Gly-Tyr-Hyp-Ser-NH$_2$;
Tyr-DArg-Phe-Sar-Tyr-Pro-Ser-NH$_2$;
Tyr-DArg-Phe-Sar-Tyr-Hyp-Ser-NH$_2$;
Tyr-DArg-Phe-Gly-Tyr-Pro-Ser-NH$_2$;
and organic or inorganic addition salts of any of said polypeptides of Group 3.

In a most preferred embodiment, the present invention provides a combination effective to cause the release and elevation of growth hormone in the blood of a mammal, the combination comprising an effective amount of polypeptides selected from at least two different groups of the Group 1 polypeptides, Group 2 polypeptides or Group 3 polypeptides set forth below.

In accordance with this most preferred embodiment of the present invention, the term "Group 1 polypeptides" is intended to include naturally occurring growth hormones, e.g., human, porcine, bovine, ovine and rat growth hormone releasing hormones, such as compounds #144–149 below, and functional analogs thereof, which polypeptides act at the growth hormone releasing hormone receptor of mammals. Compounds within this definition are selected from any of the polypeptides:

(a) having the following amino acid sequences in positions 1–44 (numbered from N terminus to C terminus):

(#144) YADAIFTNSYRKVLGQLSARKLLQDIMSRQQGESNQERGARARL-CONH$_2$ (hGHRH), (#145) YADAIFTNSYRKVLGQLSARKLLQDIMSRQQGERNQEQGARVRL-CONH$_2$ (pGHRH), (#146) YADAIFTNSYRKVLGQLSARKLLQDIMNRQQGERNQEQGAKVRL-CONH$_2$ (bGHRH), (#148) YADAIFTNSYRKILGQLSARKLLQDIMNRQQGERNQEQGAKVRL-CONH$_2$ (oGHRH), and (#149) HADAIFTSSYRRILGQLYARKLLHEIMNRQQGERNQEQRSRFN-COOH (rGHRH);

wherein the single letter abbreviations for the amino acid residues are as previously defined, including the previous definition for the C-terminal amino acid residues;

(b) any one of said (a) polypeptides having a substitution of Nle for Met at position 27;

(c) any one of said (a) or (b) polypeptides in which the N-terminus —NH$_2$ is replaced by —NHCOCH$_3$;

(d) fragments of any one of said (a), (b) or (c) polypeptides which contain at least the amino acid residues of positions 1–29, and (e) having the following amino acid sequences in positions 1–29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X, YADAIFTNCYRKVLCQLSARKLLQDIMSR-X
  (linear dithiol), and
YADAIFTNCYRKVLCQLSARKLLQDIMSR-X,
  (cyclic disulfide);
wherein the C-terminal amino acid and X are as defined above; and modification of any one of these group (e) compounds in accordance with the modifications set forth in (b), (c) and (d) above;

(f) organic or inorganic addition salts of any of said (a), (b), (c), (d) or (e) polypeptides of Group 1.

Group 2 polypeptides contemplated within this most preferred embodiment of the present invention, are selected from any of the polypeptides having the structure:
His-DTrp-Ala-Trp-DPhe-Lys-NH$_2$;
DOPA-Ala-His-DTrp-Ala-Trp-DPhe-Lys-NH$_2$;
His-DTrp-Ala-Trp-DPhe-Lys-Ala-Tyr-NH$_2$;
Lys-Ala-His-DTrp-Ala-Trp-DPhe-Lys-NH$_2$;
Tyr-Ala-His-DTrp-Ala-Trp-DPhe-Lys-NH$_2$;
Phe-Ala-His-DTrp-Ala-Trp-DPhe-Lys-NH$_2$;
Z-His-DTrp-Ala-Trp-DPhe-Lys-NH$_2$;
wherein Z is selected from the group consisting of Ala, Val, DOPA, Trp, Met, Lys, Asp, Met(O), Leu, Abu and Arg, and organic or inorganic addition salts of any of said polypeptides of Group 2; and Group 3 polypeptides contemplated within this most preferred embodiment of the present invention are selected from any of the polypeptides having the structure:
Tyr-DArg-Phe-NH$_2$;
Tyr-DAla-Phe-Gly-NH$_2$;
Tyr-DArg-Phe-Gly-NH$_2$;
Tyr-DArg-Phe-Sar;
Tyr-DAla-Gly-Phe-NH$_2$;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Phe-Gly-ol;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Gly-Tyr-DArg-Phe-Gly-NH$_2$;
Tyr-DAla-Phe-Sar-Tyr-Pro-Ser-NH$_2$;
Tyr-Dala-Phe-Gly-Tyr-Hyp-Ser-NH$_2$;
Tyr-DAla-Phe-Sar-Tyr-Hyp-Ser-NH$_2$;
Tyr-DAla-Phe-Gly-Tyr-Pro-Ser-NH$_2$;
Tyr-DArg-Phe-Gly-Tyr-Pro-Ser-NH$_2$;
Tyr-DArg-Phe-Gly-Tyr-Hyp-Ser-NH$_2$;
and organic or inorganic addition salts of any of said polypeptides of Group 3.

The invention is also concerned with a method of causing release and elevation of growth hormone in the blood of an animal, comprising administering an effective dose of a combination comprising polypeptides selected from at least two different groups of the Group 1 polypeptides, Group 2 polypeptides or Group 3 polypeptides hereinafter described in greater detail.

In accordance with the broad scope of this embodiment of the present invention, the term "Group 1 polypeptides" is intended to include naturally occurring growth hormone releasing hormones, e.g., human, porcine, ovine, and rat growth hormone releasing hormones, such as compounds #144–149 below, and functional analogs thereof. Such peptides act at the growth hormone releasing hormone receptor of mammals and other vertebrates. crustaceans and the like, to cause the release of growth hormone. Representative peptides included within this definition are selected from any of the polypeptides:

(a) having the following amino acid sequences in positions 1–44 (numbered from N terminus to C terminus):
(#144) YADAIFTNSYRKVLGQLSARKLL-QDIMSRQQGESNQERGARARL-X,
(#145) YADAIFTNSYRKVLGQLSARKLL-QDIMSRQQGERNQEQGARVRL-X,
(#146) YADAIFTNSYRKVLGQLSARKLL-QDIMNRQQGERNQEQGAKVRL-X,
(#148) YADAIFTNSYRKILGQLSARKLL-QDIMNRQQGERNQEQGAKVRL-X, and
(#149) HADAIFTSSYRRILGQLYARKL-LHEIMNRQQGERNQEQRSRFN-X;
wherein the C-terminal amino acid has the following truncated general formula:

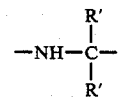

wherein each R′ independently represents the substituents of the particular amino acid residue, e.g., hydrogen, alkyl, aryl, amino or acid substituents; X denotes the C terminal end group and is selected from —CONH$_2$, —COOH, —COOR, —CONRR, —CH$_2$OH, and —CH$_2$OR, where R is an alkyl group having 1–6 carbon atoms or an aromatic ring having up to 12 carbon atoms;

(b) any one of said (a) polypeptides having the following amino acid substitutions;
position 1 of (#144–#148) is DTyr or His;
position 1 of (#149) is Tyr or DHis;
position 2 of (#144–#149) is (NMe)DAla or Aib or DAla;
position 3 of (#144–#149) is DAsp;
position 4 of (#144–#149) is DAla; and
position 1+2 of (#144–#149) is:
  DTyr$^1$+DAla$^2$,
  DTyr$^1$+(NMe)DAla$^2$, or
  DTyr$^1$+Aib$^2$;

(c) any one of said (a) or (b) polypeptides having a substitution of Nle for Met at position 27;

(d) any one of said (a), (b) or (c) polypeptides in which the N-terminus —NH$_2$ is replaced by —NHCOR and wherein R is an alkyl group having 1 to 6 carbon atoms or an aromatic ring having up to 12 carbon atoms;

(e) fragments of any one of said (a), (b), (c) or (d) polypeptides which contain at least the amino acid residues of positions 1–29;

(f) having the following amino acid sequences in positions 1–29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X
  (linear dithiol), and
YADAIFTNCYRKVLCQLSARKLLQDIMSR-X
  (cyclic disulfide):
wherein the C-terminal amino acid and X are as defined above; and modification of any one of these group (f)

compounds in accordance with the modifications set forth in (b), (c) and (d) above; and (g) organic or inorganic addition salts of any of said (a), (b), (c), (d), (e) or (f) polypeptides of Group 1.

Group 2 polypeptides contemplated within the broad scope of this embodiment of the invention are selected from any of the polypeptides having the structure:
Ala-His-DTrp-Ala-Trp-DPhe-Lys-Gly-Tyr-NH$_2$;
Ala-His-DTrp-Ser-Trp-DPhe-Lys-NH$_2$;
Ala-His-(formyl)DTrp-Ala-Trp-DPhe-Lys-NH$_2$ (DTrp is formylated at the indole nitrogen):
Cys-Ala-His-DTrp-Ala-Trp-DPhe-Lys-Cys-NH$_2$ (cyclic disulfide);
Cys-Ala-His-DTrp-Ala-Trp-DPhe-Lys-Cys-NH$_2$ (free dithiol);
DOPA-Ala-His-DTrp-Ala-Trp-DPhe-Lys-NH$_2$;
His-DTrp-Ala-Trp-DPhe-Lys-Ala-Tyr-NH$_2$;
His-DTrp-Ala-Trp-DPhe-Lys-NH$_2$;
Lys-His-DTrp-Ala-Trp-DPhe-Asp-NH$_2$;
Lys-Ala-His-DTrp-Ala-Trp-DPhe-Lys-NH$_2$;
Phe-Ala-His-DTrp-Ala-Trp-DPhe-Lys-NH$_2$;
Tyr-Ala-Gly-Thr-Ala-His-DTrp-Ala-Trp-DPhe-Lys-NH$_2$;
Tyr-Ala-His-DTrp-Ala-Trp-DPhe-Lys-NH$_2$;
Tyr-DAla-Gly-Phe-Ala-His-DTrp-Ala-Trp-DPhe-Lys-NH$_2$;
Tyr-DAla-Phe-Gly-Ala-His-DTrp-Ala-Trp-DPhe-Lys-NH$_2$;
Ala-His-XTrp*-Ala-Trp-DPhe-Lys-NH$_2$ (*XTrp is selected from the group consisting of all N-monomethylated Trp isomers, i.e., (N$^\alpha$Me)Trp, (N$^\alpha$Me)DTrp, (indole NMe)Trp and (indole NMe)DTrp);
Z-His-DTrp-Ala-Trp-DPhe-Lys-NH$_2$;
wherein Z is selected from the group consisting of all naturally occurring L-amino acids, Met(O), DOPA and Abu;
and organic or inorganic addition salts of any of said polypeptides of Group 2; and Group 3 polypeptides contemplated within the broad scope of this embodiment of the invention are selected from any of the polypeptides having the structure:
Tyr-DArg-Phe-NH$_2$;
Tyr-DAla-Phe-NH$_2$;
Tyr-DArg(NO$_2$)-Phe-NH$_2$;
Tyr-DMet(O)-Phe-NH$_2$;
Tyr-DAla-Phe-Gly-NH$_2$;
Tyr-DArg-Phe-Gly-NH$_2$;
Tyr-DThr-Phe-Gly-NH$_2$;
Phe-DArg-Phe-Gly-NH$_2$;
Tyr-DArg-Phe-Sar;
Tyr-DAla-Gly-Phe-NH$_2$;
Tyr-DArg-Gly-Trp-NH$_2$;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Tyr-DArg-Phe-Gly-ol;
Tyr-DArg-Gly-(NMe)Phe-NH$_2$;
Tyr-DArg-Phe-Sar-ol;
Tyr-DAla-Phe-Sar-ol;
Tyr-DAla-Phe-Gly-Tyr-NH$_2$;
Gly-Tyr-DArg-Phe-Gly-NH$_2$;
Tyr-DThr-Gly-Phe-Thz-NH$_2$;
Gly-Tyr-DAla-Phe-Gly-NH$_2$;
Tyr-DAla-Phe-Gly-ol;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Phe-Sar;
Tyr-DAla-Gly-(NMe)Phe-NH$_2$;
Sar-Tyr-DArg-Phe-Sar-NH$_2$;
Tyr-DCys-Phe-Gly-DCys-NH$_2$ (cyclic disulfide);
Tyr-DCys-Phe-Gly-DCys-NH$_2$ (free dithiol);
Tyr-DCys-Gly-Phe-DCys-NH$_2$ (cyclic disulfide);
Tyr-DCys-Gly-Phe-DCys-NH$_2$ (free dithiol);
Tyr-DAla-Phe-Gly-Tyr-Pro-Ser-NH$_2$;
Tyr-DAla-Phe-Sar-Tyr-Pro-Ser-NH$_2$;
Tyr-DAla-Phe-Sar-Phe-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DAla-Phe-Sar-Phe-Hyp-Ser-NH$_2$;
Tyr-DArg-Phe-Gly-Tyr-Pro-Ser-NH$_2$; and
Tyr-DArg-Phe-Gly-Tyr-Hyp-Ser-NH$_2$;
Tyr-DArg-Phe-Sar-Tyr-Pro-Ser-NH$_2$;
Tyr-DArg-Phe-Sar-Tyr-Hyp-Ser-NH$_2$;

organic or inorganic addition salts of any of said polypeptides of Group 3.

In a preferred embodiment the invention provides a method of causing release and elevation of growth hormone in the blood of an animal, comprising administering an effective dose of a combination comprising polypeptides selected from at least two different groups of the Group 1 polypeptides, Group 2 polypeptides or Group 3 polypeptides set forth below.

In accordance with this preferred embodiment of the invention method of causing release and elevation of growth hormone in the blood of a mammal or a vertebrate, the term "Group 1 polypeptides" is intended to include naturally occurring growth hormones, e.g., human, porcine, bovine, ovine and rat growth hormone releasing hormones, such as compounds #144-149 below, and functional analogs thereof, which polypeptides act at the growth hormone releasing hormone receptor of mammals and other vertebrates. Compounds within this definition are selected from any of the polypeptides:

(a) having the following amino acid sequences in positions 1-44 (numbered from N terminus to C terminus):

(#144) YADAIFTNSYRKVLGQLSARKLL-QDIMSRQQGESNQERGARARL-CONH$_2$ (hGHRH), (#145) YADAIFTNSYRKVLGQLSARKLL-QDIMSRQQGERNQEQGARVRL-CONH$_2$ (pGHRH), (#146) YADAIFTNSYRKVLGQLSARKLL-QDIMNRQQGERNQEQGAKVRL-CONH$_2$ (bGHRH), (#148) YADAIFTNSYRKILGQLSARKLL-QDIMNRQQGERNQEQGAKVRL-CONH$_2$ (oGHRH), and (#149) HADAIFTSSYRRILGQLYARKL-LHEIMNRQQGERNQEQRSRFN-COOH (rGHRH):

wherein the single letter abbreviations for the amino acid residues are as previously defined, including the previous definition for the C-terminal amino acid residues:

(b) any one of said (a) polypeptides having the following amino acid substitutions:
position 1 of (#144-#148) is DTyr or His;
position 1 of (#149) is Tyr;
position 2 of (#144-#149) is (NMe)DAla or Aib or DAla;
position 3 of (#144-#149) is DAsp;
position 4 of (#144-#149) is DAla;
position 1+2 of (#144-#149) is DTyr$^1$+DAla$^2$;

(c) any one of said (a) or (b) polypeptides having a substitution of Nle for Met at position 27;

(d) any one of said (a), (b), or (c) polypeptides in which the N-terminus —NH₂ is replaced by —NH-COCH₃; and (e) fragments of any one of said (a), (b), (c) or (d) polypeptides which contain at least the amino acid residues of positions 1-29, (f) having the following amino acid sequences in positions 1-29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X (cyclic disulfide):
wherein the C-terminal amino acid and X are as defined above; and modification of any one of these group (f) compounds in accordance with the modifications set forth in (b), (c) and (d) above; and (g) organic or inorganic addition salts of any of said (a), (b), (c), (d), (e) or (f) polypeptides of Group 1.

Group 2 polypeptides contemplated within the preferred embodiment of the invention method are selected from any of the polypeptides having the structure:
His-DTrp-Ala-Trp-DPhe-Lys-NH₂;
His-DTrp-Ala-Trp-DPhe-Lys-Ala-Tyr-NH₂;
Lys-Ala-His-DTrp-Ala-Trp-DPhe-Lys-NH₂;
Tyr-Ala-His-DTrp-Ala-Trp-DPhe-Lys-NH₂;
DOPA-Ala-His-DTrp-Ala-Trp-DPhe-Lys-NH₂;
Phe-Ala-His-DTrp-Ala-Trp-DPhe-Lys-NH₂;
Ala-His-(formyl)DTrp-Ala-Trp-DPhe-Lys-NH₂ (DTrp is formylated at the indole nitrogen):
Ala-His-DTrp-Ser-Trp-DPhe-Lys-NH₂;
Lys-His-DTrp-Ala-Trp-DPhe-Asp-NH₂;
Z-His-DTrp-Ala-Trp-DPhe-Lys-NH₂;
wherein Z is selected from the group consisting of all naturally occurring L-amino acids, Met(O), DOPA and Abu.
and organic or inorganic addition salts of any of said polypeptides of Group 2; and Group 3 polypeptides contemplated within this preferred embodiment of the invention method are selected from any of the polypeptides having the structure:
Tyr-DArg-Phe-NH₂;
Tyr-DArg(NO₂)-Phe-NH₂;
Tyr-DMet(O)-Phe-NH₂;
Tyr-DAla-Phe-Gly-NH₂;
Tyr-DArg-Phe-Gly-NH₂;
Tyr-DArg-Phe-Sar;
Tyr-DAla-Gly-Phe-NH₂;
Tyr-DAla-Gly-(NMe)Phe-Gly-ol;
Tyr-DAla-Phe-Sar-NH₂;
Tyr-DAla-Phe-Sar-NH₂;
Tyr-DArg(NO₂)-Phe-Gly-NH₂;
Tyr-DMet(O)-Phe-Gly-NH₂;
(NMe)Tyr-DArg-Phe-Sar-NH₂;
Tyr-DAla-Phe-Gly-ol;
Tyr-DAla-Phe-Gly-Tyr-NH₂;
Gly-Tyr-DArg-Phe-Gly-NH₂;
Gly-Tyr-DAla-Phe-Gly-NH₂;
Sar-Tyr-DArg-Phe-Sar-NH₂;
Tyr-DCys-Phe-Gly-DCys-NH₂ (cyclic disulfide)
Tyr-DCys-Phe-Gly-DCys-NH₂ (free dithiol);
Tyr-DCys-Gly-Phe-DCys-NH₂ (cyclic disulfide)
Tyr-DCys-Gly-Phe-DCys-NH₂ (free dithiol);
Tyr-DAla-Phe-Gly-Tyr-Pro-Ser-NH₂;
Tyr-DAla-Phe-Sar-Tyr-Pro-Ser-NH₂;
Tyr-DAla-Phe-Gly-Tyr-Hyp-Ser-NH₂;
Tyr-DAla-Phe-Sar-Tyr-Hyp-Ser-NH₂;
Tyr-DArg-Phe-Gly-Tyr-Hyp-Ser-NH₂;
Tyr-DArg-Phe-Sar-Tyr-Pro-Ser-NH₂;
Tyr-DArg-Phe-Sar-Tyr-Hyp-Ser-NH₂;
Tyr-DArg-Phe-Gly-Tyr-Pro-Ser-NH₂;
and organic or inorganic addition salts of any of said polypeptides of Group 3.

In a most preferred embodiment the invention provides a method of causing release and elevation of growth hormone in the blood of a mammal, comprising administering an effective dose of a combination comprising polypeptides selected from at least two different groups of the Group 1 polypeptides, Group 2 polypeptides or Group 3 polypeptides set forth below.

In accordance with this most preferred embodiment of the invention method, the term "Group 1 polypeptides" is intended to include naturally occurring growth hormones, e.g., human, porcine, bovine, ovine and rat growth hormone releasing hormones, such as compounds #144-149 below, and functional analogs thereof, which polypeptides act at the growth hormone releasing hormone receptor of mammals. Compounds within this definition are selected from any of the polypeptides:

(a) having the following amino acid sequences in positions 1-44 (numbered from N terminus to C terminus):
(#144) YADAIFTNSYRKVLGQLSARKLL-QDIMSRQQGESNQERGARARL-CONH₂ (hGHRH),
(#145) YADAIFTNSYRKVLGQLSARKLL-QDIMSRQQGERNQEQGARVRL-CONH₂ (pGHRH),
(#146) YADAIFTNSYRKVLGQLSARKLL-QDIMNRQQGERNQEQGAKVRL-CONH₂ (bGHRH),
(#148) YADAIFTNSYRKILGQLSARKLL-QDIMNRQQGERNQEQGAKVRL-CONH₂ (oGHRH), and
(#149) HADAIFTSSYRRILGQLYARKL-LHEIMNRQQGERNQEQRSRFN-COOH (rGHRH);
wherein the single letter abbreviations for the amino acid residues are as previously defined, including the previous definition for the C-terminal amino acid residues:

(b) any one of said (a) polypeptides having a substitution of Nle for Met at position 27;

(c) any one of said (a) or (b) polypeptides in which the N-terminus —NH₂ is replaced by —NHCOCH₃;

(d) fragments of any one of said (a), (b) or (c) polypeptides which contain at least the amino acid residues of positions 1-29;

(e) having the following amino acid sequences in position 1-29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and YADAIFTNCYRKVLCQLSARKLLQDIMSR-X (cyclic disulfide);
wherein the C-terminal amino acid and X are as defined above; and modification of any one of these group (e) compounds in accordance with the modifications set forth in (b), (c) and (d) above;

(f) organic or inorganic addition salts of any of said (a), (b), (c), (d) or (e) polypeptides of Group 1.

Group 2 polypeptides contemplated within this most preferred embodiment of the invention method are selected from any of the polypeptides having the structure:

His-DTrp-Ala-Trp-DPhe-Lys-NH$_2$;
His-DTrp-Ala-Trp-DPhe-Lys-Ala-Tyr-NH$_2$;
Lys-Ala-His-DTrp-Ala-Trp-DPhe-Lys-NH$_2$;
Tyr-Ala-His-DTrp-Ala-Trp-DPhe-Lys-NH$_2$;
DOPA-Ala-His-DTrp-Ala-Trp-DPhe-Lys-NH$_2$;
Phe-Ala-His-DTrp-Ala-Trp-DPhe-Lys-NH$_2$;
Z-His-DTrp-Ala-Trp-DPhe-Lys-NH$_2$;
wherein Z is selected from the group consisting of Ala, Val, DOPA, Trp, Met, Lys, Asp, Met(O), Leu and Arg, and
organic or inorganic addition salts of any of said polypeptides of Group 2; and Group 3 polypeptides contemplated within this most preferred embodiment of the invention method are selected from any of the polypeptides having the structure:

Tyr-DArg-Phe-NH$_2$;
Tyr-DAla-Phe-Gly-NH$_2$;
Tyr-DArg-Phe-Gly-NH$_2$;
Tyr-DArg-Phe-Sar;
Tyr-DAla-Gly-Phe-NH$_2$;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Phe-Gly-ol;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Gly-Tyr-Arg-Phe-Gly-NH$_2$;
Tyr-DAla-Phe-Sar-Tyr-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DAla-Phe-Gly-Tyr-Pro-Ser-NH$_2$;
Tyr-DArg-Phe-Gly-Tyr-Pro-Ser-NH$_2$;
Tyr-DArg-Phe-Gly-Tyr-Hyp-Ser-NH$_2$;
and organic or inorganic addition salts of any of said polypeptides of Group 3.

The invention further provides specific combinations of polypeptides and methods of using such combinations.

PREPARATION OF THE COMPOUNDS

The substances described in this invention can be synthesized according to the usual methods of solution and solid phase peptide chemistry, or by classical methods known in the art. The solid-phase synthesis is commenced from the C-terminal end of the peptide. A suitable starting material can be prepared, for instance, by attaching the required protected alpha-amino acid to a chloromethylated resin, a hydroxymethyl resin, a benzhydrylamine (BHA) resin, or a para-methyl-benzylhydrylamine (p-Me-BHA) resin. One such chloromethyl resin is sold under the tradename BIOBEADS SX-1 by Bio Rad Laboratories, Richmond, Calif. The preparation of the hydroxymethyl resin is described by Bodansky et al., Chem. Ind. (London) 38, 1597 (1966). The BHA resin has been described by Pietta and Marshall, Chem. Commn., 650 (1970) and is commercially available from Penninsula Laboratories, Inc., Belmont, Calif., or Beckman Instruments, Inc., Palo Alto, Calif., in the hydrochloric form thereof (BHA.HCl).

After the initial attachment, the alpha-amino protecting group can be removed by a choice of acidic reagents, including trifluoroacetic acid (TFA) or hydrochloric acid (HCl) solutions in organic solvents at room temperature. After removal of the alpha-amino protecting group, the remaining protected amino acids can be coupled stepwise in the desired order. Each protected amino acid can be generally reacted in about a 3-fold excess using an appropriate carboxyl group activator such as dicyclohexylcarbodiimide (DCC) in solution, for example, in methylene chloride (CH$_2$Cl$_2$) or dimethylformamide (DMF) and mixtures thereof.

After the desired amino acid sequence has been completed, the desired peptide can be cleaved from the resin support by treatment with a reagent such as hydrogen fluoride (HF) which not only cleaves the peptide from the resin, but also cleaves most commonly used side-chain protecting groups. When a chloromethyl resin or hydroxymethyl resin is used, HF treatment results in the formation of the free peptide acid. When the BHA or p-Me-BHA resin is used, HF treatment results directly in free peptide amides.

The solid-phase procedure discussed above is well known in the art and has been described by Stewart and Young, *Solid Phase Peptide Synthesis*: (Freeman and Co., San Francisco, 1969).

Some of the well known solution methods which can be employed to synthesize the peptide moieties of the instant invention are set forth in Bodansky et al., *Peptide Synthesis*, 2nd Edition, John Wiley & Sons, New York, N.Y. 1976.

COMPOSITIONS

The present invention includes within its scope compositions comprising, as an active ingredient, at least two of the compounds, or analogs thereof, described herein, or addition salts thereof, or their pharmaceutically acceptable salts in association with a carrier, diluent, slow release matrix, or coating.

The organic or inorganic addition salts of the growth hormone releasing compounds and combinations thereof contemplated to be within the scope of the present invention include salts of such organic moieties as acetate, trifluoroacetate, oxalate, valerate, oleate, laurate, benzoate, lactate, tosylate, citrate, maleate, fumarate, succinate, tartrate, naphthalate, and the like; and such inorganic moieties as Group I (i.e., alkali metal salts), Group II (i.e., alkaline earth metal salts) ammonium and protamine salts, zinc, iron, and the like with counterions such as the chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including the sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

The invention will now be described in greater detail by reference to the following non-limiting examples.

EXAMPLE 1

In Vivo GH Release in Rats

Immature female Sprague-Dawley rats were obtained from the Charles River Laboratories (Wilmington, Mass.). After arrival they were housed at 25° C. with a 14:10 hr light:dark cycle. Water and Purina rat chow were available ad libitum. Pups were kept with their mothers until 21 days of age.

Normal saline with 0.1% gelatin was the vehicle for subcutaneous (s.c.) and intravenous (i.v.) injections of the peptides. In some experiments in which the peptides were very insoluble, DMSO was used to dissolve the compounds, with dilutions then being made to the specified concentration with normal saline with 0.1% gelatin (compounds for which DMSO was needed to effect solution are so noted in the Tables). The unanesthetized rats, weighing 55-65 grams, were injected i.v. with the quantity of growth hormone releasing compounds indicated in Tables 1-4. Injection was made as a 0.2 ml solution via the tail vein. All animals were sacrificed by guillotine 10 min after the final test injection unless specified otherwise. Trunk blood for the determination of blood GH levels was collected following decapitation. The blood was allowed to clot, centrifuged and the serum separated from the clot. Serum was kept frozen until the day of sampling for radioimmunoassay (RIA) determination of growth hormone levels according to the following procedure, as developed by the National Institute of Arthritis, Diabetes and Digestive and Kidney Diseases (NIADDK).

Reagents are generally added to the RIA analysis tubes at a single sitting, at refrigerator temperature (about 4° C.) in the following sequence:
(a) buffer,
(b) "cold" (i.e., non-radioactive) standard or unknown serum sample to be analyzed,
(c) radio-iodinated growth hormone antigen, and
(d) growth hormone antiserum.

Reagent addition is generally carried out so that there is achieved a final RIA tube dilution of about 1:30,000 (antiserum to total liquid volume: vol:vol).

The mixed reagents are then typically incubated at room temperature (about 25° C.) for about 24 hours prior to addition of a second antibody (e.g., goat or rabbit anti-monkey gamma globulin serum) which binds to and causes precipitation of the complexed growth hormone antiserum. Precipitated contents of the RIA tubes are then analyzed for the number of counts in a specified period of time in a gamma scintillation counter. A standard curve is prepared by plotting number of radioactive counts v. growth hormone (GH) level. GH levels of unknowns are then determined by reference to the standard curve.

Serum GH was measured by RIA with reagents provided by the National Hormone and Pituitary Program.

Serum levels in Tables 1-4 are recorded in ng/ml in terms of the rat GH standard of 0.61 International Units/mg (IU/mg). Data is recorded as the mean $\pm/-$ standard error of the mean (SEM). Statistical analysis was performed with Student's t-test.

The results with combinations of polypeptide compounds from Groups 2 and 3 are shown in Tables 1-3. The results with combinations of polypeptide compounds from Groups 1 and 3 are shown in Table 4. The results with combinations of polypeptide compounds from Groups 1 and 2 are shown in Table 4. In each of the four Tables, the results shown are the average of studies with six rats.

TABLE 1

In Vivo GH Release (ng/ml) of Group 2 and Structurally Similar Compounds Plus Group 3 Compounds in Rats

| Number | Column A Group 2 and Structurally Similar Compounds | Dose (μg) | Control GH ng/ml | GH Released by Compound in Column A ng/ml | GH Released by #8801* (Group 3) | Compound in Column A + #8801* (Groups 2 & 3) | GH Released by #9218* (Group 3) | Compound in Column A + #9218* (Groups 2 & 3) |
|---|---|---|---|---|---|---|---|---|
| 8310 | DAla—His—DTrp—Ala—Trp—DPhe—Lys—NH2** | 100 | 3 ± 0.5 | 16 ± 2 | | 313 ± 100(b) | | |
| 8937 | (beta)Ala—His—DTrp—Ala—Trp—DPhe—Lys—NH2** | 10 | 10 ± 1.4 | 32 ± 4 | 49 ± 7(a) | 87 ± 35(a) | | |
| 8588 | Ala—His—DPal—Ala—Trp—DPhe—Lys—NH2** | 100 | 8 ± 8 | 19 ± 5 | 109 ± 36(b) | 115 ± 27(b) | | |
| 8323 | Ala—His—DTrp—Ala—Pal—DPhe—Lys—NH2** | 100 | 3 ± 0.5 | 18 ± 1 | | 421 ± 101(b) | | |
| 9308 | Ala—Cys—DTrp—Ala—Trp—DPhe—Lys—Cys—NH2** | 10 | 14 ± 2.0 | 10 ± 1 | | | 178 ± 78 | 98 ± 11 |
| 9887 | Ala—His—DTrp—Ala—Trp—DPhe—Lys—Cys—NH2** | 10 | 13 ± 1.0 | 11 ± 1 | | | 161 ± 63 | 27 ± 4 |
| 9090 | DPgl—Lys—NH2** Ala—His—DTrp—Ala—Trp—DPhe—Lys—DLys—NH2** | 10 | 7 ± 2.0 | 14 ± 3 | 68 ± 4(a) | 78 ± 13(a) | | |
| 10265 | Ala—His—DArg—Ala—Trp—DPhe—Lys—NH2** | 10 | 13 ± 2(b) | 14 ± 2 | | | 229 ± 26 | 364 ± 165 |
| 10351 | DDopa—Ala—His—DTrp—Ala—Trp—DPhe—Lys—NH2**** | 10 | 12 ± 2 | 13 ± 2 | | | 135 ± 27 | 288 ± 62 |
| 8758 | Cys—Ala—His—DTrp—Ala—Trp—DPhe—Lys—Cys—NH2*** | 10 | 8.0 ± 2.0 | 37 ± 8 | 398 ± 196(a) | 1070 ± 211(a) | | |
| 8758 | Cys—Ala—His—DTrp—Ala—Trp—DPhe—Lys—Cys—NH2** | 10 | 14.0 ± 2.0 | 26 ± 9 | | | 178 ± 78(a) | 588 ± 152(a) |
| 8114 | Ala—His—DTrp—Ala—Trp—DPhe—Lys—NH2 | 10 | 3.0 ± 0.5 | 93 ± 30 | 648 ± 176(b) | 1143 ± 270(b) | | |
| 8114 | Ala—His—DTrp—Ala—Trp—DPhe—Lys—NH2 | 10 | 17.0 ± 3.0 | 129 ± 46 | | | | |
| 8114 | Ala—His—DTrp—Ala—Trp—DPhe—Lys—NH2 | 10 | 10.0 ± 1.4 | 52 ± 8 | 49 ± 7(a) | 791 ± 50(a) | | |
| 8114 | Ala—His—DTrp—Ala—Trp—DPhe—Lys—NH2 | 10 | 7.0 ± 2.0 | 54 ± 7 | 68 ± 4(a) | 746 ± 43(a) | | |
| 8114 | Ala—His—DTrp—Ala—Trp—DPhe—Lys—NH2 | 10 | 12.0 ± 1.0 | 72 ± 9 | 37 ± 12(a) | 172 ± 6(a) | | |
| 8114 | Ala—His—DTrp—Ala—Trp—DPhe—Lys—NH2 | 10 | 14.0 ± 2.0 | 119 ± 28 | | | 178 ± 78(a) | 2697 ± 427(a) |
| 8114 | Ala—His—DTrp—Ala—Trp—DPhe—Lys—NH2 | 10 | 7.3 ± 2.0 | 55 ± 13 | 43 ± 8(a) | 1155 ± 288(a) | 32 ± 10(a) | 1633 ± 679(a) |
| 8114 | Ala—His—DTrp—Ala—Trp—DPhe—Lys—NH2 | 10 | 2.2 ± 0.6 | 152 ± 40 | 92 ± 31(b) | 1490 ± 245(a) | | |
| 8114 | Ala—His—DTrp—Ala—Trp—DPhe—Lys—NH2 | 10 | 18.0 ± 11.0 | | 149 ± 62(a) | 2035 ± 472(a) | 131 ± 67(a) | 1223 ± 384(a) |
| 8114 | Ala—His—DTrp—Ala—Trp—DPhe—Lys—NH2 | 10 | 14.0 ± 1.0 | 132 ± 36 | 54 ± 16(a) | 1265 ± 284(a) | 38 ± 9(a) | 566 ± 25(a) |
| 8114 | Ala—His—DTrp—Ala—Trp—DPhe—Lys—NH2 | 10 | 9.0 ± 4.0 | 105 ± 37 | | | 205 ± 29(a) | 1472 ± 307(a) |
| 8114 | Ala—His—DTrp—Ala—Trp—DPhe—Lys—NH2 | 10 | 7.0 ± 0.6 | 117 ± 36 | 309 ± 88(b) | 1386 ± 224(b) | | |
| 8114 | Ala—His—DTrp—Ala—Trp—DPhe—Lys—NH2 | 10 | 2.0 ± 0.2 | 115 ± 50 | 448 ± 175(b) | 1176 ± 347(a) | | |

TABLE 1-continued

In Vivo GH Release (ng/ml) of Group 2 and Structurally Similar Compounds Plus Group 3 Compounds in Rats

| Number | Column A Group 2 and Structurally Similar Compounds | Dose (μg) | Control GH ng/ml | GH Released by Compound in Column A ng/ml | GH Released by #8801* (Group 3) | Compound in Column A + #8801* (Groups 2 & 3) | GH Released by #9218* (Group 3) | Compound in Column A + #9218* (Groups 2 & 3) |
|---|---|---|---|---|---|---|---|---|
| 8114 | Ala—His—DTrp—Ala—Trp—DPhe—Lys—NH2 | 10 | 6.0 ± 0.7 | 169 ± 60 | 60 ± 16(a) | 1390 ± 419(a) | | |
| 8114 | Ala—His—DTrp—Ala—Trp—DPhe—Lys—NH2 | 10 | 9.0 ± 1.0 | 210 ± 42 | | | 49 ± 9(a) | 1589 ± 313(a) |
| 8114 | Ala—His—DTrp—Ala—Trp—DPhe—Lys—NH2 | 10 | 18.0 ± 3.0 | 255 ± 73 | | | 367 ± 79(a) | 1921 ± 284(a) |
| 8114 | Ala—His—DTrp—Ala—Trp—DPhe—Lys—NH2 | 10 | 10.0 ± 1.0 | 315 ± 65 | | | 177 ± 53(a) | 1169 ± 269(a) |
| 8114 | Ala—His—DTrp—Ala—Trp—DPhe—Lys—NH2 | 10 | 30.0 ± 1.0 | 114 ± 20 | | | 226 ± 70(a) | 2006 ± 333(a) |
| 8866 | Tyr—Ala—Gly—Thr—Ala—His—DTrp—Ala—Trp—DPhe—Lys—NH2 | 10 | 8.0 ± 2.0 | 177 ± 38 | 398 ± 196(a) | 1698 ± 281(a) | | |
| 8866 | Tyr—Ala—Gly—Thr—Ala—His—DTrp—Ala—Trp—DPhe—Lys—NH2 | 30 | 8.0 ± 2.0 | 144 ± 38 | 398 ± 196(a) | 1130 ± 172(a) | | |
| 8866 | Tyr—Ala—Gly—Thr—Ala—His—DTrp—Ala—Trp—DPhe—Lys—NH2 | 10 | 14.0 ± 1.0 | 292 ± 42 | | | 38 ± 9(a) | 1567 ± 350(a) |
| 9106 | Tyr—DAla—Phe—Gly—Ala—His—DTrp—Ala—Trp—DPhe—Lys—NH2 | 100 | 14.0 ± 1.0 | 116 ± 42 | | | 38 ± 9(a) | 1227 ± 348(a) |
| 9216 | Tyr—DAla—Gly—Phe—Ala—His—DTrp—Ala—Trp—DPhe—Lys—NH2 | 30 | 12.0 ± 1.0 | 46 ± 12 | 37 ± 12(a) | 506 ± 174(a) | | |
| 9216 | Tyr—DAla—Gly—Phe—Ala—His—DTrp—Ala—Trp—DPhe—Lys—NH2 | 100 | 14.0 ± 1.0 | 196 ± 43 | | | 38 ± 9(a) | 1365 ± 276(a) |
| 8938 | His—DTrp—Ala—Trp—DPhe—Lys—NH2 | 10 | 3.0 ± 0.5 | 70 ± 29 | 648 ± 176(b) | 2375 ± 312(b) | | |
| 9036 | His—DTrp—Ala—Trp—DPhe—Lys—Ala—Tyr—NH2 | 10 | 10.0 ± 1.0 | 52 ± 7 | | | 177 ± 53(a) | 873 ± 201(a) |
| 9020 | Abu—His—DTrp—Ala—Trp—DPhe—Lys—NH2 | 10 | 18.0 ± 11.0 | 85 ± 24 | | | 131 ± 67(a) | 1770 ± 444(a) |
| 9868 | DOPA—Ala—His—DTrp—Ala—Trp—DPhe—Lys—NH2 | 10 | 13.0 ± 1.0 | 123 ± 30 | | | 161 ± 63(a) | 1791 ± 284(a) |
| 10276 | Leu—His—DTrp—Ala—Trp—DPhe—Lys—NH2 | 10 | 13.0 ± 2(b) | 190 ± 58 | | | 229 ± 26 | 1748 ± 233 |
| 10276 | Leu—His—DTrp—Ala—Trp—DPhe—Lys—NH2 | 10 | 13.0 ± 1.0 | 74 ± 25 | | | 166 ± 44 | 1602 ± 403 |
| 10321 | Val—His—DTrp—Ala—Trp—DPhe—Lys—NH2 | 10 | 13.0 ± 2(b) | 137 ± 28 | | | 229 ± 26 | 3093 ± 382 |
| 10337 | Phe—Ala—His—DTrp—Ala—Trp—DPhe—Lys—NH2 | 10 | 12.0 ± 2.0 | 68 ± 11 | | | 135 ± 27 | 1049 ± 203 |
| 10337 | Phe—Ala—His—DTrp—Ala—Trp—DPhe—Lys—NH2 | 10 | 14.0 ± 2.0 | 132 ± 45 | | | | 2855 ± 642 |
| 10391 | Ala—His—DTrp—Ala—Trp—DPhe—Lys—Gly—Tyr—NH2 (c) | 10 | 12.0 ± 2.0 | 36 ± 6 | | | 135 ± 27 | 1830 ± 583 |
| 10391 | Ala—His—DTrp—Ala—Trp—DPhe—Lys—Gly—Tyr—NH2 (c) | 10 | 14.0 ± 2.0 | 155 ± 59 | | | 135 ± 27 | 1544 ± 554 |
| 10321 | Val—His—DTrp—Ala—Trp—DPhe—Lys—NH2 | 1 | 5.0 ± 0.4 | 11 ± 2 | | | 223 ± 95 | 464 ± 76 |
| 10321 | Val—His—DTrp—Ala—Trp—DPhe—Lys—NH2 | 3 | 5.0 ± 0.4 | 129 ± 13 | | | 223 ± 95 | 849 ± 134 |

TABLE 1-continued

In Vivo GH Release (ng/ml) of Group 2 and Structurally Similar Compounds Plus Group 3 Compounds in Rats

| Number | Column A Group 2 and Structurally Similar Compounds | Dose (μg) | Control GH ng/ml | GH Released by Compound in Column A ng/ml | GH Released by #8801* (Group 3) | Compound in Column A + #8801* (Groups 2 & 3) | GH Released by #9218* (Group 3) | Compound in Column A + #9218* (Groups 2 & 3) |
|---|---|---|---|---|---|---|---|---|
| 10321 | Val—His—DTrp—Ala—Trp—DPhe—Lys—NH₂ | 10 | 5.0 ± 0.4 | 68 ± 29 | | | 223 ± 95 | 1259 ± 286 |
| 10855 | Ala—His—(formyl)DTrp—Ala—Trp—DPhe—Lys—NH₂ | 10 | 6.0 ± 1.0 | 19 ± 6 | | | 144 ± 46 | 558 ± 154 |
| 10814 | Dopa—His—DTrp—Ala—Trp—DPhe—Lys—NH₂ | 3 | 6.0 ± 1.0 | 67 ± 17 | | | 144 ± 46 | 1427 ± 418 |
| 10814 | Dopa—His—DTrp—Ala—Trp—DPhe—Lys—NH₂ | 10 | 6.0 ± 1.0 | 76 ± 20 | | | 144 ± 46 | 3631 ± 459 |
| 10957 | Trp—His—DTrp—Ala—Trp—DPhe—Lys—NH₂ (d) | 10 | 7.0 ± 1.0 | 127 ± 23 | | | 107 ± 21 | 1819 ± 243 |
| 10957 | Trp—His—DTrp—Ala—Trp—DPhe—Lys—NH₂ (d) | 30 | 7.0 ± 1.0 | 268 ± 58 | | | 107 ± 21 | 2293 ± 319 |
| 10873 | Met—His—DTrp—Ala—Trp—DPhe—Lys—NH₂ (d) | 10 | 7.0 ± 1.0 | 65 ± 18 | | | 107 ± 21 | 2005 ± 428 |
| 10873 | Met—His—DTrp—Ala—Trp—DPhe—Lys—NH₂ (d) | 30 | 7.0 ± 1.0 | 161 ± 47 | | | 107 ± 21 | 2052 ± 577 |
| 10973 | Ala—His—DTrp—Ser—Trp—DPhe—Lys—NH₂ (d) | 10 | 7.0 ± 0.5 | 30 ± 7 | | | 156 ± 39 | 558 ± 131 |
| 11009 | Lys—His—DTrp—Ala—Trp—DPhe—Lys—NH₂ (d) | 3 | 5.0 ± 0.4 | 57 ± 9 | | | 115 ± 57 | 1063 ± 231 |
| 11009 | Lys—His—DTrp—Ala—Trp—DPhe—Lys—NH₂ (d) | 10 | 5.0 ± 0.4 | 217 ± 64 | | | 115 ± 57 | 1514 ± 322 |
| 11012 | Asp—His—DTrp—Ala—Trp—DPhe—Lys—NH₂ (d) | 10 | 7.0 ± 0.5 | 128 ± 48 | | | 156 ± 39 | 1267 ± 306 |
| 11012 | Asp—His—DTrp—Ala—Trp—DPhe—Lys—NH₂ | 10 | 12.0 ± 0.5 | 107 ± 26 | | | 110 ± 55 | 1052 ± 174 |
| 18988 | Met(O)—His—DTrp—Ala—Trp—DPhe—Lys—NH₂ | 10 | 14.0 ± 0.5 | 65 ± 17 | | | 173 ± 52 | 2126 ± 420 |
| 18988 | Met(O)—His—DTrp—Ala—Trp—DPhe—Lys—NH₂ | 3 | 5.0 ± 0.4 | 90 ± 25 | | | 115 ± 57 | 1448 ± 183 |
| 11553 | Tyr—Ala—His—DTrp—Ala—Trp—DPhe—Lys—NH₂ | 10 | 6.5 ± 0.5 | 170 ± 38 | | | 252 ± 46 | 2354 ± 469 |
| 11561 | Lys—His—DTrp—Ala—Trp—DPhe—Asp—NH₂ | 3 | 8.0 ± 1.0 | 9 ± 1 | | | 84 ± 37 | 444 ± 167 |
| 11561 | Lys—His—DTrp—Ala—Trp—DPhe—Asp—NH₂ | 10 | 8.0 ± 1.0 | 11 ± 1 | | | 84 ± 37 | 530 ± 237 |
| 11562 | Arg—His—DTrp—Ala—Trp—DPhe—Lys—NH₂ | 3 | 8.0 ± 1.0 | 50 ± 17 | | | 84 ± 37 | 473 ± 53 |
| 11562 | Arg—His—DTrp—Ala—Trp—DPhe—Lys—NH₂ | 10 | 8.0 ± 1.0 | 87 ± 27 | | | 84 ± 37 | 1448 ± 319 |
| 11603 | Lys—Ala—His—DTrp—Ala—Trp—DPhe—Lys—NH₂ | 3 | 16.0 ± 3.0 | 41 ± 5 | | | 170 ± 42 | 1008 ± 272 |
| 11603 | Lys—Ala—His—DTrp—Ala—Trp—DPhe—Lys—NH₂ | 10 | 16.0 ± 3.0 | 82 ± 19 | | | 170 ± 42 | 1437 ± 226 |
| 11603 | Lys—Ala—His—DTrp—Ala—Trp—DPhe—Lys—NH₂ | 30 | 16.0 ± 3.0 | 135 ± 38 | | | 170 ± 42 | 1859 ± 214 |

TABLE 1-continued

In Vivo GH Release (ng/ml) of Group 2 and Structurally Similar Compounds Plus Group 3 Compounds in Rats

| Number | Column A Group 2 and Structurally Similar Compounds | Dose (μg) | Control GH ng/ml | GH Released by Compound in Column A ng/ml | GH Released by #8801* (Group 3) | Compound in Column A + #8801* (Groups 2 & 3) | GH Released by #9218* (Group 3) | Compound in Column A + #9218* (Groups 2 & 3) |
|---|---|---|---|---|---|---|---|---|
| | DPhe—Lys—NH$_2$ | | | | | | | |

*#8801 is Tyr—DAla—Phe—Gly—Tyr—Pro—Ser—NH$_2$ and #9218 is Tyr—DArg—Phe—Gly—NH$_2$

**compounds so designated are structurally similar to the Group 2 compounds defined in the text, but do not display the synergistic response promoted by compounds within Group 2.

***contains cyclic disulfide bridge between Cys groups (a) 30 μg dose
(b) 100 μg dose
(c) Group 2 compound initially dissolved in 10 mM acetic acid
(d) Group 2 compound initially dissolved in 10 DMSO

TABLE 2
In Vivo Synergistic Effects of Heptapeptide Group 3 Compounds Acting with #8114 (Group 2) in Rats

| Number | Column A Group 3 Compounds | Amount (μg) | Control (ng/ml) | GH Release (ng/ml) by Compounds in Column A | GH Release (ng/ml) by #8114 (Group 2) | GH Release (ng/ml) by Compound in Column A Plus 10 μg #8114 (Group 2) |
|---|---|---|---|---|---|---|
| 8754 | Tyr—DAla—(NMe)Phe—Gly—Tyr—Pro—Ser—NH2 | 30 | 12 ± 1.0 | 15 ± 3 | 72 ± 9 | 156 ± 35 |
| 8801 | Tyr—DAla—Phe—Gly—Tyr—Pro—Ser—NH2 | 100 | 3.0 ± 0.5 | 60 ± 17 | 93 ± 30 | 715 ± 75 |
| 8801 | Tyr—DAla—Phe—Gly—Tyr—Pro—Ser—NH2 | 100 | 7.0 ± 0.6 | 309 ± 88 | 117 ± 36 | 1386 ± 224 |
| 8801 | Tyr—DAla—Phe—Gly—Tyr—Pro—Ser—NH2 | 100 | 7.0 ± 0.6 | 279 ± 76 | 117 ± 36 | 1292 ± 271 |
| 8801 | Tyr—DAla—Phe—Gly—Tyr—Pro—Ser—NH2 | 30 | 14.0 ± 1.0 | 54 ± 16 | 132 ± 36 | 1265 ± 284 |
| 8801 | Tyr—DAla—Phe—Gly—Tyr—Pro—Ser—NH2 | 30 | 7.3 ± 2.0 | 43 ± 8 | 55 ± 13 | 1155 ± 228 |
| 8801 | Tyr—DAla—Phe—Gly—Tyr—Pro—Ser—NH2 | 30 | 7.0 ± 2.0 | 68 ± 4 | 54 ± 7 | 746 ± 43 |
| 8846 | Tyr—DAla—Phe—Sar—Tyr—Pro—Ser—NH2 | 30 | 3.8 ± 0.5 | 32 ± 7 | 210 ± 71 | 906 ± 214 |
| 8846 | Tyr—DAla—Phe—Sar—Tyr—Pro—Ser—NH2 | 30 | 18.0 ± 11.0 | 22 ± 7 | | 468 ± 125 |
| 8924 | Tyr—DAla—Phe—Sar—Phe—Pro—Ser—NH2 | 30 | 10.0 ± 1.4 | 45 ± 5 | 52 ± 8 | 362 ± 51 |
| 8802 | Tyr—DAla—Phe—Gly—Tyr—Hyp—Ser—NH2 | 100 | 17.0 ± 3.0 | 308 ± 101 | 129 ± 46 | 874 ± 179 |
| 8802 | Tyr—DAla—Phe—Gly—Tyr—Hyp—Ser—NH2 | 100 | 7.0 ± 0.6 | 215 ± 66 | 117 ± 36 | 1761 ± 232 |
| 9292 | Tyr—DArg—Phe—Gly—Tyr—Pro—Ser—NH2 | 30 | 7.3 ± 2.0 | 17 ± 3 | 55 ± 13 | 448 ± 124 |
| 9292 | Tyr—DArg—Phe—Gly—Tyr—Pro—Ser—NH2 | 30 | 18.0 ± 11.0 | 44 ± 20 | | 855 ± 190 |

TABLE 3
In Vivo Synergistic Effects of Group 3 and Structurally Similar Compounds with #8114 (Group 2) in Rats

| Number | Column A Group 3 and Structurally Similar Compounds | Amount (μg) | Control (ng/ml) | GH Release (ng/ml) by Compounds in Column A | GH Release (ng/ml) by #8114 (Group 2) | GH Release (ng/ml) by Compound in Column A + 10 μg #8114 (Group 2) |
|---|---|---|---|---|---|---|
| 8680 | Tyr—DAla—NH2* | 100 | 2.4 ± 0.5 | 12 ± 3 | | 203 ± 99 |
| 8346 | Tyr—DAla—Phe—NH2 | 100 | 3 ± 0.5 | 21 ± 2 | 93 ± 30 | 249 ± 71 |
| 8346 | Tyr—DAla—Phe—NH2 | 100 | 2.4 ± 0.5 | 22 ± 9 | | 325 ± 150 |
| 8346 | Tyr—DAla—Phe—NH2 | 30 | 7 ± 2 | 23 ± 7 | 258 ± 48 | 386 ± 44 |
| 8346 | Tyr—DAla—Phe—NH2 | 100 | 7 ± 2 | 11 ± 4 | 258 ± 48 | 773 ± 174 |
| 9224 | Tyr—DLys—Phe—Gly—NH2* | 30 | 7.3 ± 2.0 | 19 ± 2 | 55 ± 13 | 71 ± 4 |
| 9227 | Tyr—DHis—Phe—Gly—NH2 | 30 | 7.3 ± 2.0 | 21 ± 4 | 55 ± 13 | 238 ± 76 |
| 9222 | His—DArg—Phe—Gly—NH2* | 30 | 7.3 ± 2.0 | 17 ± 2 | 55 ± 13 | 80 ± 14 |
| 8734 | Tyr—DAla—Phe—Met—NH2* | 100 | 17 ± 2.0 | 17 ± 2 | | 27 ± 7 |
| 9962 | Tyr—DArg—DOPA—GlyNH2* | 30 | 22.0 ± 2.0 | 15 ± 2 | 54 ± 14 | 113 ± 42 |
| 52-4 | Tyr(OMe)—DAla—Phe—Gly—ol* | 30 | 22.0 ± .9 | | 105 ± 37 | 116 ± 36 |
| 10010 | Tyr—Arg(NO2)—Phe—Gly—NH2* | 30 | 9 ± 0.5 | 10 ± 2 | 122 ± 49 | 203 ± 58 |
| 11415 | Tyr—DAla—Phe—Gly—(NMe)Tyr—NH2* | 30 | 9 ± .3 | 29 ± 3 | 159 ± 29 | 200 ± 74 |
| 8796 | Tyr—DAla—Phe—Gly—Tyr—Pro—NH2* | 30 | 3.8 ± 0.5 | 2 ± 0.7 | 210 ± 71 | 211 ± 24 |
| 8319 | Tyr—DAla—Phe—Gly—NH2 | 100 | 3.0 ± 0.5 | 60 ± 17 | 93 ± 30 | 715 ± 75 |
| 8319 | Tyr—DAla—Phe—Gly—NH2 | 100 | 2.4 ± 0.5 | 96 ± 36 | 129 ± 35 | 667 ± 159 |
| 9218 | Tyr—DArg—Phe—Gly—NH2 | 3 | 9.0 ± 1.0 | 11 ± 1 | 210 ± 42 | 442 ± 50 |
| 9218 | Tyr—DArg—Phe—Gly—NH2 | 10 | 9.0 ± 1.0 | 27 ± 6 | 210 ± 42 | 917 ± 151 |
| 9218 | Tyr—DArg—Phe—Gly—NH2 | 30 | 9.0 ± 1.0 | 49 ± 9 | 210 ± 42 | 1589 ± 313 |
| 8338 | Tyr—DThr—Phe—Gly—NH2 | 100 | 3.0 ± 0.5 | 32 ± 61 | 93 ± 30 | 329 ± 95 |
| 9259 | Phe—DArg—Phe—Gly—NH2 | 30 | 7.3 ± 2.0 | 23 ± 6 | 55 ± 13 | 240 ± 74 |
| 9651 | Tyr—DArg—Phe—Sar—NH2 | 3 | 9.0 ± 1.0 | 43 ± 16 | 210 ± 42 | 350 ± 89 |
| 9651 | Tyr—DArg—Phe—Sar—NH2 | 10 | 9.0 ± 1.0 | 66 ± 16 | 210 ± 42 | 666 ± 148 |
| 10467 | Tyr—DArg—Phe—NH2 | 30 | 10.0 ± 1.0 | 15 ± 4 | 125 ± 32 | 621 ± 135 |
| 10467 | Tyr—DArg—Phe—NH2 | 100 | 13.0 ± 1.0 | 45 ± 11 | 166 ± 44 | 1028 ± 180 |
| 9651 | Tyr—DArg—Phe—Sar—NH2 | 30 | 9.0 ± 1.0 | 45 ± 11 | 210 ± 42 | 1413 ± 214 |
| 9367 | Tyr—DArg—Phe—Sar—COOH | 30 | 18.0 ± 3.0 | 51 ± 16 | 255 ± 73 | 1140 ± 236 |
| 8677 | Tyr—DAla—Gly—Phe—NH2 | 100 | 3.0 ± 0.5 | 41 ± 11 | 93 ± 30 | 975 ± 223 |
| 8925 | Tyr—DAla—Gly—(NMe)Phe—NH2 | 30 | 10.0 ± 1.4 | 36 ± 4 | 52 ± 8 | 442 ± 99 |
| 9254 | Tyr—DAla—Gly—Trp—NH2 | 30 | 14.0 ± 1.0 | 12 ± 2 | 132 ± 36 | 552 ± 87 |
| 8678 | Tyr—DThr—Gly—Phe—Thz—NH2 | 100 | 2.2 ± 0.6 | 49 ± 28 | 152 ± 40 | 654 ± 208 |
| 8678 | Tyr—DThr—Gly—Phe—Thz—NH2 | 100 | 2.4 ± 0.5 | 57 ± 11 | 129 ± 35 | 764 ± 237 |
| 8777 | Tyr—DAla—Phe—Gly—Tyr—NH2 | 30 | 3.8 ± 0.5 | 25 ± 9 | 210 ± 71 | 483 ± 107 |
| 8818 | Tyr—DAla—Gly—(NMe)Phe—Gly-ol | 100 | 2.2 ± 0.6 | 145 ± 65 | 152 ± 40 | 1586 ± 234 |
| 9585 | Gly—Tyr—DArg—Phe—Gly—NH2 | 30 | 10.0 ± 1.0 | 35 ± 9 | 315 ± 65 | 589 ± 179 |
| 8625 | Tyr—DAla—Gly(NMe)Phe—Met(O)—ol | 100 | 17.0 ± 3.0 | 252 ± 61 | 129 ± 46 | 1881 ± 142 |
| 1898 | Tyr—DAla—Phe—Gly—ol | 30 | 18 ± 3.0 | 16 ± 0.8 | 255 ± 73 | 345 ± 123 |
| 1898 | Tyr—DAla—Phe—Gly—ol | 100 | 18 ± 3.0 | 15 ± 2.0 | 255 ± 73 | 782 ± 105 |
| 10224 | Tyr—DArg(NO2)—Phe—Gly—NH2 | 30 | 13 ± 2.0 | 22 ± 4.0 | 53 ± 14 | 747 ± 206 |
| 10409 | Tyr—DAla—Phe—Sar—NH2 | 30 | 14 ± 2.0 | 114 ± 9.0 | 125 ± 32 | 1222 ± 265 |
| 10467 | Tyr—DArg—Phe—NH2 | 30 | 10 ± 1.0 | 15 ± 4.0 | 125 ± 32 | 621 ± 135 |
| 10467 | Tyr—DArg—Phe—NH2 | 100 | 13 ± 1.0 | 45 ± 11 | 166 ± 44 | 1028 ± 180 |
| 11385 | Tyr—DMet(O)—Phe—Gly—NH2 | 30 | 9 ± 3.0 | 590 ± 201 | 159 ± 29 | 1471 ± 343 |
| 11385 | Tyr—DMet(O)—Phe—Gly—NH2 | 30 | 6.5 ± 0.5 | 747 ± 248 | 92 ± 8 | 2413 ± 391 |
| 11416 | NMe—Tyr—DArg—Phe—Sar—NH2 | 30 | 9 ± 3.0 | 116 ± 24 | 159 ± 29 | 1477 ± 221 |
| 8777 | Tyr—DAla—Phe—Gly—Tyr—NH2 | 30 | 3.8 ± 0.5 | 25 ± 9 | 210 ± 71 | 483 ± 107 |
| 9585 | Gly—Tyr—DArg—Phe—Gly—NH2 | | 22.0 ± 2.0 | 67 ± 21 | 54 ± 14 | 1682 ± 176 |

TABLE 3-continued
In Vivo Synergistic Effects of Group 3 and Structurally Similar Compounds with #8114 (Group 2) in Rats

| Number | Column A Group 3 and Structurally Similar Compounds | Amount (µg) | Control (ng/ml) | GH Release (ng/ml) by Compounds in Column A | GH Release (ng/ml) by #8114 (Group 2) | GH Release (ng/ml) by Compound in Column A + 10 µg #8114 (Group 2) |
|---|---|---|---|---|---|---|
| 9585 | Gly—Tyr—DArg—Phe—Gly—NH$_2$ | 100 | 22.0 ± 2.0 | 270 ± 24 | 54 ± 14 | 2318 ± 468 |
| 10390 | Sar—Tyr—DArg—Phe—Sar—NH$_2$ | 30 | 12.0 ± 2.0 | 15 ± 2 | 211 ± 61 | 510 ± 126 |
| 10863 | Tyr—DCys—Phe—Gly—DCys—NH$_2$ (cyclic disulfide) | 30 | 7.0 ± 1.0 | 48 ± 21 | 188 ± 40 | 795 ± 171 |
| 10863 | Tyr—DCys—Phe—Gly—DCys—NH$_2$ (cyclic disulfide) | 100 | 7.0 ± 1.0 | 334 ± 102 | 188 ± 40 | 1917 ± 276 |
| 10910 (a) | Tyr—DCys—Gly—Phe—DCys—NH$_2$ (cyclic disulfide) | 30 | 7.0 ± 1.0 | 18 ± 7 | 188 ± 40 | 418 ± 115 |
| 10910 (a) | Tyr—DCys—Gly—Phe—DCys—NH$_2$ (cyclic disulfide) | 100 | 7.0 ± 1.0 | | 188 ± 40 | 980 ± 159 |

*Compounds so designed are structurally similiar to the Group 3 compounds defined in the text, but do not display the synergistic response promoted by compounds within Group 3.
(a) DMSO employed to solubilize Group 3 compound

TABLE 4
In Vivo Synergistic Effects of GHRH and Its Analogs (Group 1) with the Group 2 and Group 3 Compounds in Rats

| Group 1 Compounds* | Amount (µg) | Control | GH Release (ng/ml) by Group 1 Compounds | GH Release (ng/ml) by Group 1 Compound plus 10 µg #8114 (Group 2) | GH Release (ng/ml) by Group 1 Compound plus 30 µg #8801 (Group 3) | GH Release (ng/ml) by Group 1 Compound plus 30 µg #9218 (Group 3) | GH Release (ng/ml) by Group 1 Compound plus x µg #8114 (Group 2) plus y µg #9218 (Group 3) | GH Release (ng/ml) by Group 1 Compound plus 10 µg #8114 (Group 2) plus 30 µg #8801 |
|---|---|---|---|---|---|---|---|---|
| #8686 | 1 | 2.0 ± 0.2 | 64 ± 16 | | | | | |
| #8686 | 3 | 2.0 ± 0.2 | 105 ± 23 | | | | | |
| #8686 | 10 | 9.0 ± 1.0 | 114 ± 21 | | | | | |
| #8686 | 10 | 2.0 ± 0.2 | 165 ± 17 | | 1060 ± 149 | | 1744 ± 177(a) | |
| #8686 | 10 | 30.0 ± 1.0 | 282 ± 47 | 1136 ± 138 | | | 2816 ± 162(a) | 1882 ± 255 |
| #8686 | 3 | 22.0 ± 9.0 | | | | | 2420 ± 305(b) | |
| #8686 | 3 | 9.0 ± 1.0 | | | | | 1660 ± 278(b) | |
| #10363 | 10 | 6 ± 0.7 | 124 ± 19 | 772 ± 232 | | | | 2083 ± 403 |
| #10363 | 3 | 14 ± 1.0 | 62 ± 8 | | | 1689 ± 264 | | |
| #10363 | 10 | 14 ± 1.0 | 99 ± 11 | | | 3733 ± 515 | | |
| #10363 | 30 | 14 ± 1.0 | 132 ± 24 | | | 2652 ± 560 | | |
| #10363 | 10 | 10 ± 0.2 | 105 ± 29 | | | 2241 ± 323 | | |
| #10286 | 10 | 13 ± 2.0 | 145 ± 41 | | | 3314 ± 275 | | |
| #10286 | 30 | 13 ± 2.0 | 151 ± 33 | | | 2875 ± 472 | | |
| #10286 | 100 | 13 ± 2.0 | 374 ± 94 | | | 2328 ± 297 | | |
| #10286 | 10 | 10 ± 0.2 | 77 ± 10 | | | 2078 ± 395 | | |
| #11120 | 3 | 14 ± 5.0 | 151 ± 29 | | | 3689 ± 521 | | |

(a) x = 10, y = 10
(b) x = 3, y = 3
*Formulas of the various Group 1 compounds are set out on the next page.
8686 is Nle$^{27}$#144(1-29)NH$_2$ which is Tyr—Ala—Asp—Ala—Ile—Phe—Thr—Asn—Ser—Tyr—Arg—Lys—Val—Leu—Gly—Gln—Leu—Ser—Ala—Lys—Leu—Leu—Gln—Asp—Ile—Nle—Ser—Arg—NH$_2$
10363 is Cys$^9$, Cys$^{15}$, Nle$^{27}$ #144(1-29)NH$_2$ which is Tyr—Ala—Asp—Ala—Ile—Phe—Thr—Asn—Cys—Tyr—Arg—Lys—Val—Leu—Cys—Gln—Leu—Ser—Ala—Arg—Lys—Leu—Leu—Gln—Asp—Ile—Nle—Ser—Arg—NH$_2$ (cyclic disulfide)
10286 is Cys$^9$, Cys$^{15}$, Nle$^{27}$ #144(1-29)NH$_2$ which is Tyr—Ala—Asp—Ala—Ile—Phe—Thr—Asn—Cys—Tyr—Arg—Lys—Val—Leu—Cys—Gln—Leu—Ser—Ala—Arg—Lys—Leu—Leu—Gln—Asp—Ile—Nle—Ser—Arg—NH$_2$ (linear disulfide)
11120 is DAla$^2$, Nle$^{27}$ #144(1-29)NH$_2$ which is Tyr—DAla—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Ser—Arg—NH$_2$ In Table 1, Group 2 compounds are shown to act synergistically with two different Group 3 compounds. Several different assays of the compound, #8114, with compounds #8801 and/or #9218 are shown, in which synergism is evident. Many additional combinations of Group 2 compounds were also assayed when administered in combination with compounds #8801 and/or #9218. In every case for Group 2 compounds, when the amount of GH released by the individual compound is added to the amount of GH released by the second compound when given alone, the result is far less than the amount of GH released when the two compounds have been administered to the rat either simultaneously, or at different locations on the rat. Thus, synergism is seen for all such combinations. It is also clear that the synergism observed is not a function of premixing the compounds, but is a result of their combined action on the GH releasing mechanism, requiring both compounds to be present to exert the remarkable synergistic effect.

Several examples are also presented in Table 1 of compounds which are structurally similar to, but outside the definition of Group 2 compounds set forth in the text. The first nine entries in Table 1, denoted by **, which are all structurally similar to the Group 2 compounds, display no synergistic response when administered in combination with either compound #8801 or #9218. It is thus seen that the surprising synergistic response observed in the practice of the present invention is not a general phenomenon, but is instead obtained only with specific compounds as set forth in the text under the definition of Group 1, Group 2 and Group 3 polypeptides.

In Tables 2 and 3, we show the enhanced release of GH into the blood caused by a number of different tetra-, penta-, and heptapeptides of Group 3 in combination with #8114 (Group 2). Even low dosages are shown to achieve synergistic responses. Also shown in Table 3 are a number of compounds (those denoted by *) which are structurally similar to the Group 3 compounds, but which do not exhibit a synergistic response in combination with Group 1 and/or Group 2 compounds. These results demonstrate that the surprising synergistic response observed in the practice of the present invention is obtained only with specific compounds as set forth in the text.

Table 4 shows the results of combining members of Groups 1 and 2, Groups 1 and 3, and all three groups of compounds together. Since the response to the three-component combination is well above the sum of the three individual responses, low doses effect significant GH responses. In fact, at equal doses of 3 μg (3+3+3) as shown in Table 4, one would expect a release of only several hundred ng/ml of GH released if the result were only additive. However, the three-component mixture actually caused release of approximately 2000 ng/ml of GH at these low dosages.

EXAMPLE 2

Rat Growth Study

In Table 5 is shown a study in which the rats were treated for ten days using a combination of His-DTrp-Ala-Trp-DPhe-Lys-NH$_2$ (compound #8938, Group 2) +hGHRH (Human Growth Hormone Releasing Hormone; compound #144-NH$_2$, see Group 1). Saline or 10 μg each of #8938+#144-NH$_2$ was administered once daily via the tail vein to conscious female rats. Injections were begun when the rats were 21 days of age.

Table 5. Effects of Once Daily i.v. Treatment with #8938+#144-NH$_2$ on Body Weight in Rats.

TABLE 5

| Day | Body Weight (Gm +/− SEM) | |
|---|---|---|
| | Saline | #8938 + #144-NH$_2$ |
| 1 | 40.1 +/− 1.2 | 42.8 +/− 1.1 |
| 2 | 42.6 +/− 1.1 | 46.3 +/− 1.2 |
| 3 | 45.1 +/− 1.2 | 51.0 +/− 1.3* |
| 4 | 49.4 +/− 1.4 | 54.7 +/− 1.3* |
| 5 | 53.2 +/− 1.3 | 60.9 +/− 1.4** |
| 6 | 57.5 +/− 1.5 | 64.4 +/− 1.6** |
| 7 | 60.2 +/− 1.6 | 68.9 +/− 1.9** |
| 8 | 62.8 +/− 1.5 | 72.7 +/− 1.8** |
| 9 | 67.3 +/− 1.8 | 76.9 +/− 1.8** |
| 10 | 72.9 +/− 1.8 | 81.4 +/− 1.9** |

*p < .05
**p < .01 vs saline treated control animals

The body weight change of 11.7% increase over control is conclusive evidence for the effect of the combination therapy.

EXAMPLE 3

In Vivo Growth Hormone Release Study—Lambs

Female lambs (17–22 kg) were housed in individual cages in a constant temperature room at 24° C. with 12h-12h light-dark cycle. The lambs were fed a maintenance diet containing chick cracked corn (43.3%), soybean meal (7.1%), cottonseed hulls (38.1%), molasses (8.6%) and premix consisting of vitamins and minerals (2.9%).

Various doses of the dermorphin (compound #8801) in combination with various doses of compound #8114 were mixed and dissolved in 200 μl of 10mM acetic acid and brought to 5 ml with phosphate buffered saline (PBS). Lambs were catheterized via the jugular vein. Intravenous infusions were performed by using a multi-channel infusion pump (Model 600-900, Harvard Apparatus Co., Inc., Dover, Mass.) preset at a flow rate of 1.36 ml/min. Sampling of blood was performed every 20 minutes starting 1 hour prior to treatment and continuing until 3–4 hours after treatment. Additional samples were taken at −10 min., +5 min. and +10 min. Blood samples were drawn and deposited into EDTA-treated tubes for plasma preparation. EDTA treated plasma was analyzed for GH using a standard double antibody RIA, according to the following procedure:

---

PROCEDURE FOR LAMB GROWTH HORMONE RADIOIMMUNMOASSAY

Reagents

1. Phosphosaline Buffer (0.15 M NaCl-0.012 M Phosphate) (PSB):
   Add 5.14 gm NaH$_2$PO$_4$.H$_2$O (monobasic) and 26.6 gm sodium chloride to 2.95 liters distilled water.
   Add 2.0 M sodium hydroxide dropwise to bring pH to 7.5.
   Add 3 ml merthiolate as preservative.
   Bring total volume to 3.0 liters.
   Store at 4° C.
2. Phosphosaline Buffer With 1% Bovine Serum Albumin (PBSA):
   Dilute commercially available 30% solution of bovine serum albumin (BSA) thirtyfold with phosphosaline buffer (PSB).
   Store at 4° C. and use without further dilution.
3. Ovine Growth Hormone Antiserum (rabbit):
   Stored frozen at 1:10 dilution (as obtained).
   Working dilution is 1:20,000. Prepare only enough dilution to last one week. Store at 4° C.
4. Ovine Growth Hormone:
   Prepare and store frozen in vials (2.5 μg/0.5 ml PBSA/vial).
5. Radioiodinated Ovine Growth Hormone (Approximately 10,000 cpm/100 μl).
6. Goat Anti-Rabbit Gamma Globulin (suggested sources, Antibodies, Inc., Cambridge Medical Diagnostics, Inc.)
   Stored frozen in 1 ml aliquots.
7. 6% PEG in PSB:
   Weight 6.0 gm Polyethylene Glycol 6000.
   Dilute to 100 ml in PSB (see 1).
   Store at 4° C.
8. 0.05 M EDTA:
   Weight 1.9 gm (Ethylenedinitrilo)-tetraacetic Acid Tetrasodium Salt,
   Dilute to 100 ml in PSB (see 1).
   Adjust pH to 7.5 with NaOH.
   Store at 4° C.
9. Normal Rabbit Serum:
   Store frozen in 1.0 ml aliquots.
10. Normal Rabbit Serum:EDTA (1:400) (NRS:EDTA):
    Dilute 0.25 ml NRS to 100 ml with 0.05 M EDTA (see 8):
    Store at 4° C.

Assay Procedure (for 250 Tubes)

DAY 1

1. Label 12 × 75 mm glass tubes as follows:
   Tubes 1-2 (to be used to measure nonspecific binding NSB).
   Tubes 3-4 (to be used to measure maximum binding B$_o$).
   Tubes 5-6 (to be used to measure total counts).

PROCEDURE FOR LAMB GROWTH HORMONE RADIOIMMUNMOASSAY

Tubes 7-18 (to be used for standards A-F). Starting with tube 19, two tubes are consecutively numbered for each control or sample.

2. Add 4.5 ml PBSA to 2.5 μg/0.5 ml stock ovine growth hormone. (The concentration is now 500 ng/ml)
   Continue to dilute standards as follows:
   A - 0.25 ng/100 μl → dilute D 1/10 (100 μl + 900 μl PBSA)
   B - 0.5 ng/100 μl → dilute E 1/10 (100 μl + 900 μl PBSA)
   C - 1 ng/100 μl → dilute F 1/10 (100 μl + 900 μl PBSA)
   D - 2.5 ng/100 μl → dilute stock 1/20 (50 μl + 950 μl PBSA)
   E - 5 ng/100 μl → dilute stock 1/10 (100 μl + 900 μl PBSA)
   F - 10 ng/100 μl → dilute stock 1/5 (200 μl + 800 μl PBSA)
3. Dilute ovine growth hormone antiserum (1:10 dilution) to 1:20,000 (25 μl antiserum + 49.98 ml 1:400 NRS:EDTA).
4. Add 200 μl NRS:EDTA + 500 μl PBSA to tubes 1 and 2. (to determine NSB).
5. Add 500 μl PBSA to tubes 3 and 4. (to determine $B_o$).
6. Add 100 μl of Standards A through F, controls or samples as follows:

| Tube No. | Standards, Controls or Samples |
|---|---|
| 7,8 | A |
| 9,10 | B |
| 11,12 | C |
| 13,14 | D |
| 15,16 | E |
| 17,18 | F |
| Sample | Unknown |

7. Add 400 μl PBSA to standards A-F and all samples
8. Add 200 μl of diluted ovine growth hormone antiserum to all tubes except NSB (1 and 2) and total counts (5 and 6).
9. Vortex tubes, cover tubes and incubate at 40° C. for 20 hours.

DAY 2

9. Add 100 μl of radioiodinated ovine growth hormone to all tubes. (Approximately 10,000 cpm/100 μl.) Vortex tubes and incubate at 4° C. for 20 hours.

DAY 3

10. Dilute goat anti-rabbit gamma globulin to 1:10 or as stated on container with PBSA.
    Add 200 μl of diluted goat anti-rabbit gamma globulin to all tubes (except tubes 5 and 6). Vortex tubes and incubate at room temperature for 15 minutes.
11. Add 1 ml 6% PEG in PSB to all tubes (except tubes 5 and 6). Vortex and centrifuge at 1500-1600 g for 25 minutes.
12. Measure precipitate for radioactivity counts using an LKB Model 1275 gamma-scintillation counter.

Iodination grade ovine GH was obtained from the National Pituitary Center, and was used for iodination (Chloramine T method) and standard. The anti-ovine GH serum was also obtained from the National Pituitary Center. The results are presented in Tables 6 and 7.

TABLE 6

Plasma GH Concentration (ng/ml) in Sheep*
Treated with Group 2 + Group 3 Heptapeptides

| Compound | #8114 (Group 2) | #8801 (Group 3) | #8114 (Group 2) + #8801 (Group 3) | #8114 (Group 2) + #8801 (Group 3) | #8114 (Group 2) + #8801 (Group 3) | #8114 (Group 2) + #8801 (Group 3) |
|---|---|---|---|---|---|---|
| Dosage (μg/kg Body Weight) | 2.67 | 2.67 | 2.67 + 2.67 | 2.67 + 0.33 | 0.33 + 2.67 | 0.33 + 0.33 |
| Time (min) | | | | | | |
| −10 | 7 | 15 | 9 | 18 | 9 | 11 |
| 0 | 6 | 10 | 8 | 19 | 9 | 5 |
| +5 | 8 | 5 | 60 | 58 | 10 | 2 |
| +10 | 14 | 8 | — | 78 | 11 | 4 |
| +20 | 9 | 2 | 76 | 62 | 11 | 2 |

*All values are the mean of two animals.

TABLE 7

Plasma GH Concentration (ng/ml) in Sheep*
Treated with Group 1 + Group 2 + Group 3 Compounds

| Compound | #8114 (Group 2) | #8801 (Group 3) | #8686 (Group 1) | #8801 (Group 3) + #8686 (Group 1) | #8114 (Group 2) + #8801 (Group 3) + #8686 (Group 1) |
|---|---|---|---|---|---|
| Dosage (μg/kg Body Weight) | 5.5 | 5.5 | 5.5 | 5.5 + 5.5 | 5.5 + 5.5 + 5.5 |
| Time (min) | | | | | |
| −10 | 2 | 17 | 2 | 1 | 3 |
| 0 | 1 | 2 | 2 | 2 | 4 |
| +5 | 2 | 4 | 75 | 70 | 158 |
| +10 | 3 | 3 | 100 | 100 | 225 |
| +20 | 1 | 10 | 68 | 87 | 168 |

*All values are the mean of two animals.

In Tables 6 and 7 a Group 2 compound (#8114) is shown to act synergistically with a Group 3 compound (#8801) in the sheep. Each assay shown is an average result of studies on two sheep. In each case, when an effective dose of the combination is administered to the animal together, the resulting amount of growth hormone released is far greater than the amount of growth hormone released by #8114 and #8801 when given individually.

EXAMPLE 4

In Vivo Growth Hormone Release Study—Goats

Lactating female goats (46–60 kg) were housed in individual cages in a constant temperature room at 24° C. with 12h-12h light-dark cycle. The goats were fed a commercial goat chow containing 16% crude protein, 3.25% crude fat and 8% crude fiber and alfalfa hay.

A mixture of 5.87 μg/kg body weight of compound #8801 and identical quantity of compound #8114 was dissolved in 10mM acetic acid and brought to 5 ml with phosphate buffered saline. Goats were catheterized via the jugular vein. Intravenous infusions of the entire 5 ml of phosphate buffered saline solution were performed by using a multichannel infusion pump (Model 600-900, Harvard Apparatus Co., Inc., Dover, Mass.) preset at a flow rate of 1.36 ml/min. Blood GH levels were determined as described in the previous example. The results are presented in Table 8.

TABLE 8

Plasma GH Concentration (ng/ml) of Lactating Goats Treated with #8114 (Group 2) Plus #8801 (Group 3) Compounds Each at 5.87 μg per kg Body Weight

| Time (min) | GH (ng/ml) Mean of 4 Animals ± SEM |
|---|---|
| −10 | 10.8 ± 0.3 |
| 0 | 11.8 ± 0.3 |
| +5 | 71.4 ± 0.9 |
| +10 | 70.4 ± 1.4 |
| +20 | 42.4 ± 1.8 |
| +40 | 16.9 ± 0.7 |
| +60 | 8.5 ± 0.3 |

The enhanced levels of serum growth hormone levels at times of +5 up to +40 minutes compared to serum growth hormone levels at times of −10 and 0 (control value) provides strong evidence for the beneficial effect of administration of the combination of growth hormone releasing compounds (#8114 and #8801) to lactating ruminant mammals.

EXAMPLE 5

In Vivo Growth Hormone Release Study—Primates

The synergistic release of growth hormone caused by Group 1, Group 2 and Group 3 compounds was examined in male and female subhuman primates. The weight range for the female rhesus monkeys was 5.5±0.3 kg and 7.8±0.5 kg for the males. The ages of the females were 8.0±1.2 yrs and the males were 8.7±0.9 yrs. The monkeys were maintained on a diet of Purina Hi Pro Monkey Chow.

After an overnight fast the animals were anesthetized between 9:00 and 11:30 a.m. with ketamine hydrochloride at a dosage of 10 mg/kg body weight. In equal dosages of 15, 40, 120 or 360 μg each, compound #144-NH$_2$ (Group 1), compound #8938 (Group 2) and compound #8801 (Group 3) were administered to groups ranging from 6–18 adult male and 6–21 female rhesus monkeys.

Blood was drawn at 0 time and the test peptides injected i.v. via a sterile butterfly inserted into a saphenous vein. The test peptides were dissolved in 0.1% sterile gelatin saline and injected in 0.5 ml volume. Blood was then collected at +10 and +20 minutes after the injection via the same vein. All animals were observed for one hour after injection.

The serum was allowed to clot and frozen until analyzed for GH. The samples were assayed for GH with an ICN (Immuno Nuclear) human GH (hGH) kit obtained from Immuno Nuclear Corporation, Stillwater, Minn. The results were read against the hGH kit standard (1.0–30 ng/ml) and appropriate dilutions were made with assay buffer when necessary.

Results are presented in Tables 9 and 10.

TABLE 9

GH Release in Female Rhesus Monkey

| No. of Animals/Group | Peptide | Dosage (μg each peptide) | 0 | +10 | +20 |
|---|---|---|---|---|---|
| | | | GH ng/ml ± SEM | | |
| 6 | Control | | 3 ± 2 | 9 ± 6 | 9 ± 7 |
| 6 | #8938 | 40 | 2 ± 1 | 4 ± 2 | 3 ± 1 |
| 6 | #8938 | 120 | 12 ± 9 | 84 ± 36 | 68 ± 30 |
| 6 | #8938 | 360 | 6 ± 3 | 65 ± 21 | 69 ± 19 |
| 6 | #144-NH$_2$ | 40 | 6 ± 3 | 7 ± 2 | 8 ± 2 |
| 7 | #8801 | 40 | 6 ± 2 | 6 ± 2 | 5 ± 1 |
| 7 | #144-NH$_2$ + #8938 | 40 | 8 ± 3 | 36 ± 9 | 34 ± 12 |
| 21 | #8938 + #8801 | 40 | 3 ± 1 | 35 ± 8 | 39 ± 10 |
| 6 | #8938 + #8801 | 120 | 2 ± 1 | 57 ± 24 | 58 ± 23 |
| 14 | #144-NH$_2$ + #8801 | 40 | 7 ± 2 | 13 ± 3 | 10 ± 3 |
| 12 | #8938 + #8801 + #144-NH$_2$ | 15 | 4 ± 1 | 47 ± 9 | 32 ± 6 |
| 12 | #8938 + #8801 + #144-NH$_2$ | 40 | 5 ± 2 | 62 ± 11 | 53 ± 11 |
| 5 | #8938 + #8801 + #144-NH$_2$ | 120 | 6 ± 3 | 38 ± 7 | 62 ± 16 |

TABLE 10

GH Release in Male Rhesus Monkey

| No. of Animals/Group | Peptide | Dosage (μg each peptide) | 0 | +10 | +20 |
|---|---|---|---|---|---|
| | | | GH ng/ml ± SEM | | |
| 6 | Control | | 1 ± 0.4 | 2 ± 1 | 3 ± 2 |
| 6 | #8938 | 40 | 2 ± 0.4 | 2 ± 0.7 | 3 ± 1 |
| 6 | #8938 | 120 | 2 ± 0.7 | 40 ± 12 | 72 ± 14 |
| 6 | #8938 | 360 | 3 ± 1 | 46 ± 13 | 105 ± 9 |

TABLE 10-continued

GH Release in Male Rhesus Monkey

| No. of Animals/Group | Peptide | Dosage (μg each peptide) | Time (Minutes) 0 | +10 | +20 |
|---|---|---|---|---|---|
| | | | GH ng/ml ± SEM | | |
| 6 | #144-NH$_2$ | 40 | 4 ± 1 | 8 ± 3 | 10 ± 3 |
| 6 | #8801 | 40 | 7 ± 3 | 6 ± 2 | 6 ± 3 |
| 6 | #8938 + #144-NH$_2$ | 40 | 2 ± 1 | 16 ± 10 | 23 ± 9 |
| 18 | #8938 + #8801 | 40 | 5 ± 1 | 32 ± 8 | 53 ± 8 |
| 6 | #8938 + #8801 | 120 | 7 ± 2 | 64 ± 20 | 74 ± 15 |
| 12 | #144-NH$_2$ + #8801 | 40 | 4 ± 1 | 5 ± 1 | 7 ± 1 |
| 12 | #8938 + #144-NH$_2$ + #8801 | 15 | 2.34 ± 0.2 | 18 ± 7 | 19 ± 8 |
| 12 | #8938 + #144-NH$_2$ + #8801 | 40 | 4 ± 1 | 37 ± 7 | 60 ± 9 |
| 6 | #8938 + #144-NH$_2$ + #8801 | 120 | 7 ± 2 | 108 ± 25 | 121 ± 18 |

In Tables 9 and 10 various binary and ternary combinations of a compound from Group 1 (#144-NH$_2$), Group 2 (#8938) and Group 3 (#8801) are shown to act synergistically to release growth hormone in either the male or female monkey. The total number of animals in each test group is indicated in the individual table.

EXAMPLE 6

In Vivo Growth Hormone Release Study—Rats

The synergistic effect of the same combination of Group 1, Group 2 and Group 3 compounds as was tested in Example 5 for causing the release growth hormone in rhesus monkeys was again tested, this time in male and female rats. The experimental protocol set forth in Example 1 was employed for these tests. Results are presented in Tables 11 and 12.

TABLE 11

GH Release in 26 Day Old Female Rats

| Peptide | Dosage μg IV | RGH ng/ml ± SEM | p Value |
|---|---|---|---|
| — | — | 11 ± 6 | |
| #8938 | 1 | 21 ± 4 | |
| | 3 | 58 ± 26 | |
| | 10 | 233 ± 88 | |
| #144-NH$_2$ | 1 | 57 ± 6 | |
| | 3 | 74 ± 10 | |
| | 10 | 97 ± 14 | |
| #8938 + #144-NH$_2$ | 1 + 1 | 159 ± 36 | — |
| | 3 + 3 | 298 ± 78 | — |
| | 10 + 10 | 1184 ± 195 | — |
| #8801 | 3 | 29 ± 5 | |
| | 10 | 39 ± 5 | |
| | 30 | 37 ± 9 | |
| #8938 + #144-NH$_2$ + #8801 | 3 + 3 + 3 | 1532 ± 337 | <.01 |
| | 3 + 10 + 10 | 1523 ± 365 | NS |
| | 10 + 1 + 1 | 1172 ± 252 | <.01 |
| | 10 + 3 + 3 | 1497 ± 288 | <.01 |
| | 10 + 10 + 10 | 1844 ± 177 | <.05 |
| | 30 + 1 + 1 | 1746 ± 425 | <.01 |
| | 30 + 3 + 3 | 1870 ± 206 | <.001 |

Mean of 6 ± SEM; p Value vs respective control

TABLE 12

GH Release in 26 Day Old Male Rats

| Peptide | Dosage μg IV | RGH ng/ml ± SEM | p Value |
|---|---|---|---|
| — | — | 3 ± 1.7 | |
| #8938 | 1 | 11 ± 6 | |
| | 3 | 31 ± 11 | |
| | 10 | 287 ± 69 | |
| | 30 | 233 ± 81 | |
| #144-NH$_2$ | 1 | 26 ± 8 | |
| | 3 | 80 ± 11 | |
| | 10 | 102 ± 19 | |
| | 30 | 184 ± 66 | |
| #8938 + #144-NH$_2$ | 10 + 10 | 1063 ± 343 | |
| #8801 | 100 | 25 ± 9 | |
| #8938 + #8801 | 10 + 100 | 2714 ± 277 | <.01 |
| #144-NH$_2$ + #8801 | 10 + 100 | 1827 ± 401 | <.001 |
| #8938 + #144-NH$_2$ + #8801 | 10 + 10 + 100 | 4473 ± 363 | — |

Mean of 6 ± SEM; p Value vs respective control

In Tables 11 and 12 various binary and ternary combinations of a compound from Group 1 (#144-NH$_2$), Group 2 (#8938) and Group 3 (#8801) are shown to act synergistically to release growth hormone in either the male or female rat. Each assay shown is the average result of studies on six rats.

The data set forth in Tables 9–12 clearly demonstrate that the synergistic effect of the combination of the Group 1 compound (#144-NH$_2$), the Group 2 compound (#8938) and the Group 3 compound (#8801) is not dependent upon the individual species being examined, nor upon the sex of the animal being examined. Instead, the synergistic response to combinations in accordance with the present invention is seen to be broadly applicable with respect to species and gender.

Various dosage combinations of any two or all three of the above peptides (i.e., #144-NH$_2$, #8938 and #8801) showed a dramatic synergistic response in both the subhuman primate (both male and female) and the rat (both male and female).

EXAMPLE 7

In Vivo Growth Hormone Release Study—Cows

Four non-lactating Holstein cows (mean body weight 543 kg) were housed outside in pasture and brought into the large animal laboratory for experimental studies in conventional stanchions. Cow diet was hay, grass and 1x/day 5 lbs. of Omolene (wheat, oats, corn, soybean, molasses with vitamins and trace minerals)—Purina. Cows were in the large animal laboratory and off grass for 1-1.5 hours before initiation of experiments. Catheters were inserted into the jugular vein for withdrawal of blood samples and IV injections of peptides. Fifteen to twenty ml of saline was flushed through the catheter after each blood drawing and a slow IV [i.v. ?] drip of saline was used to keep the blood from clotting in the catheter. Ten ml blood samples were collected between 9 AM and 2 PM at −40, −30, −10, 0, +5, +10, +15, +20, +25, +30, +40, +60, +90, +120, +150, +180. Normal saline with 0.1% gelatin or peptides dissolved in 0.1% gelatin saline was injected IV through the catheter at 0 time to the unanesthetized cows. The saline/peptide was infused over a 3 minute period in a 5.0 volume. The blood was allowed to clot, centrifuged and the serum separated from the clot. Serum was kept frozen until the day of sampling for radioimmunoassay (RIA) of growth hormone. Serum GH was measured by RIA with reagents provided by the NIADDK. The GH levels are reported in terms of ng/ml of a bovine GH reference preparation, NIH-GH-B18, which is equivalent to 3.2 IU/mg. Data is recorded as the mean± the standard error of the mean (SEM). Statistical analysis was performed with the Student's t-test.

TABLE 13

GH Release in Non-Lactating Holstein Cows

| Peptide | Dosage µg IV | RGH ng/ml ± SEM | p Value vs 1 | p Value vs 2 |
|---|---|---|---|---|
| 1 Control | | 0.17 ± 0.19 | — | <.001 |
| 2 #9218 | 3 | 2.10 ± 0.51 | <.01 | <.01 |
| 3 #8686 | 3 | 5.70 ± 0.58 | <.001 | <.02 |
| 4 #8114 | 3 | 8.60 ± 2.50 | <.01 | NS |
| 5 #8114 + #9218 | 3 + 3 | 17.60 ± 4.60 | <.001 | — |
| 6 #8114 + #9218 + #8686 | 3 + 3 + 3 | 60.00 ± 9.70 | <.001 | <.001 |
| 7 #8114 + #8686 | 3 + 3 | 88.00 ± 19.00 | <.001 | ~.001 |

Studies performed in 4 cows (mean 543 kg BW).
Calculation of Δ mean value
(1) Mean GH baseline (4 samples before saline or peptide) minus GH level at each time period after saline or peptide = Δ$^1$ GH values.
(2) All Δ$^1$ GH values of each treatment group (12 samples) were averages = Δ$^2$ mean GH ng/ml serum ± SEM.
Mean of 6 ± SEM; p Value vs respective control The data presented in Table 13 demonstrates the synergistic response in a non-lactating dairy cow for combinations of Group 1 plus Group 2 compounds; Group 2 plus Group 3 compounds; and Group 1 plus Group 2 plus Group 3 compounds.

The invention has been described in detail with particular reference to preferred embodiments thereof, but it will be understood that variations and modifications can be effected within the spirit and scope of the invention.

We claim:

1. A composition effective to cause the release and elevation of the level of growth hormone in the blood of an animal, the composition comprising an effective amount of polypeptides selected from at least two different groups of Group 1 polypeptides, Group 2 polypeptides or Group 3 polypeptides. In a ratio such that such composition is effective to cause the synergistic release and elevation of growth hormone in the blood of such animal;
wherein Group 1 polypeptides are selected from any of the mutually occurring growth hormone releasing hormones and functional equivalents thereof, wherein said polypeptides act at the growth hormone releasing hormone receptor of mammals and other vertebrates, and crustaceans;

Group 2 polypeptides are selected from any of the polypeptides having the structure:
Ala-His-DTrp-Ala-Trp-DPhe-Lys-Gly-Tyr-NH$_2$;
Ala-His-(formyl)DTrp-Ala-Trp-DPhe-Lys-NH$_2$ (DTrp is formylated at the indole nitrogen);
Ala-His-DTrp-Ser-Trp-DPhe-Lys-NH$_2$;
Cys-Ala-His-DTrp-Ala-Trp-DPhe-Lys-Cys-NH$_2$ (cyclic disulfide);
Cys-Ala-His-DTrp-Ala-Trp-DPhe-Lys-Cys-NH$_2$ (free dithiol);
DOPA-Ala-His-DTrp-Ala-Trp-DPhe-Lys-NH$_2$;
His-DTrp-Ala-Trp-DPhe-Lys-NH$_2$;
His-DTrp-Ala-Trp-DPhe-Lys-Ala-Tyr-NH$_2$;
Lys-Ala-His-DTrp-Ala-Trp-DPhe-Lys-NH$_2$;
Lys-His-DTrp-Ala-Trp-DPhe-Asp-NH$_2$;
Phe-Ala-His-DTrp-Ala-Trp-DPhe-Lys-NH$_2$;
Tyr-Ala-Gly-Thr-Ala-His-DTrp-Ala-Trp-DPhe-Lys-NH$_2$;
Tyr-Ala-His-DTrp-Ala-Trp-DPhe-Lys-NH$_2$;
Tyr-DAla-Phe-Gly-Ala-His-DTrp-Ala-Trp-DPhe-Lys-NH$_2$;
Tyr-DAla-Gly-Phe-Ala-His-DTrp-Ala-Trp-DPhe-Lys-NH$_2$;
Ala-His-XTrp*-Ala-Trp-DPhe-Lys-NH$_2$ (*XTrp is selected from the group consisting of all N-monomethylated Trp isomers, i.e., (N$^\alpha$Me)Trp, (N$^\alpha$Me)DTrp, (indole NMe)Trp and (indole NMe)DTrp);
Z-His-DTrp-Ala-Trp-DPhe-Lys-NH$_2$;
wherein Z is selected from the group consisting of all naturally occurring L-amino acids, Met(O), DOPA and Abu;
and organic or inorganic addition salts of any of said polypeptides of Group 2; and Group 3 polypeptides are selected from any of the polypeptides having the structure:
Tyr-DArg-Phe-NH$_2$;
Tyr-DAla-Phe-NH$_2$;
Tyr-DArg(NO$_2$)-Phe-NH$_2$;
Tyr-DMet(O)-Phe-NH$_2$;
Tyr-DAla-Phe-Gly-NH$_2$;
Tyr-DArg-Phe-Gly-NH$_2$;
Tyr-DThr-Phe-Gly-NH$_2$;
Phe-DArg-Phe-Gly-NH$_2$;
Tyr-DArg-Phe-Sar;
Tyr-DAla-Gly-Phe-NH$_2$;
Tyr-DArg-Gly-Trp-NH$_2$;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Tyr-DArg-Phe-Gly-ol;
Tyr-DArg-Gly-(NMe)Phe-NH$_2$;
Try-DArg-Phe-Sar-ol
Tyr-DAla-Phe-Sar-ol
Tyr-DAla-Phe-Gly-Tyr-NH$_2$;
Gly-Tyr-DArg-Phe-Gly-NH$_2$;
Tyr-DThr-Gly-Phe-Thz-NH$_2$;
Gly-Tyr-DAla-Phe-Gly-NH$_2$;
Tyr-DAla-Phe-Gly-ol;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Phe-Sar;
Tyr-DAla-Gly-(NMe)Phe-NH$_2$;
Sar-Tyr-DArg-Phe-Sar-NH$_2$;
Tyr-DCys-Phe-Gly-DCys-NH$_2$ (cyclic disulfide);
Tyr-DCys-Phe-Gly-DCys-NH$_2$ (free dithiol);
Tyr-DCys-Gly-Phe-DCys-NH$_2$ (cyclic disulfide);
Tyr-DCys-Gly-Phe-DCys-NH$_2$ (free dithiol);
Tyr-DAla-Phe-Gly-Tyr-Pro-Ser-NH$_2$;
Tyr-DAla-Phe-Sar-Tyr-Pro-Ser-NH$_2$;
Tyr-DAla-Phe-Sar-Phe-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DAla-Phe-Sar-Phe-Hyp-Ser-NH$_2$;
Tyr-DArg-Phe-Gly-Tyr-Hyp-Ser-NH$_2$;
Tyr-DArg-Phe-Sar-Tyr-Pro-Ser-NH$_2$;
Tyr-DArg-Phe-Sar-Tyr-Hyp-Ser-NH$_2$;

Tyr-DArg-Phe-Gly-Tyr-Pro-Ser-NH₂; and organic or inorganic addition salts of any of said polypeptides of Group 3.

2. Composition of claim 1 wherein said Group 1 polypeptides are selected from any of the polypeptides:
(a) having the following amino acid sequences in positions 1-44 (numbered from N terminus to C terminus):
(#144)    YADAIFTNSYRKVLGQLSARKLL-QDIMSRQQGESNQERGARARL-X,
(#145)    YADAIFTNSYRKVLGQLSARKLL-QDIMSRQQGERNQEQGARVRL-X,
(#146)    YADAIFTNSYRKVLGQLSARKLL-QDIMNRQQGERNQEQGAKVRL-X,
(#148)    YADAIFTNSYRKILGQLSARKLL-QDIMNRQQGERNQEQGAKVRL-X,
(#149)    HADAIFTSSYRRILGQLYARKL-LHEIMNRQQGERNQEQRSRFN-X; and functional equivalents thereof;
wherein the C-terminal amino acid has the following truncated general formula:

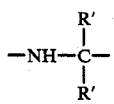

wherein each R' independently represents the substituents of the particular amino acid residue, e.g.; hydrogen, alkyl, aryl, amino or acid substituents; X denotes the C terminal end group and is selected from —CONH₂, —COOH, —COOR, —CONRR, —CH₂OH, and —CH₂OR, where R is an alkyl group having 1-6 carbon atoms or an aromatic ring having up to 12 carbon atoms; and wherein the amino acid residue abbreviations used are in accordance with the standard peptide nomenclature:
G=Gly (Glycine),
Y=Tyr (L-Tyrosine),
I=Ile (L-Isoleucine),
E=Glu (L-Glutamic Acid),
T=Thr (L-Threonine),
F=Phe (L-Phenylalanine),
A=Ala (L-Alanine),
K=Lys (L-Lysine),
D=Asp (L-Aspartic Acid),
C=Cys (L-Cysteine),
R=Arg (L-Arginine),
Q=Gln (L-Glutamine),
P=Pro (L-Proline),
L=Leu (L-Leucine),
M=Met (L-Methionine),
S=Ser (L-Serine),
N=Asn (L-Asparagine),
H=His (L-Histidine),
W=Trp (L-Tryptophan), and
V=Val (L-Valine);
(b) any one of said (a) polypeptides having the following amino acid substitutions:
position 1 of (#144–#148) is DTyr or His;
position 1 of (#149) is Tyr or DHis;
position 2 of (#144–#149) is (NMe)DAla or Aib or DAla;
position 3 of (#144–#149) is DAsp;
position 4 of (#144–#149) is DAla; and
position 1+2 of (#144–#149) is;

DTyr¹+DAla², DTyr¹+(NMe)DAla², or DTyr¹+Aib²;
(c) any one of said (a) or (b) polypeptides having a substitution of Nle for Met at position 27;
(d) any one of said (a), (b) or (c) polypeptides in which the N-terminus —NH₂ is replaced by —NHCOR and wherein R is an alkyl group having 1 to 6 carbon atoms, or an aromatic ring having up to 12 carbon atoms;
(e) fragments of any one of said (a), (b), (c) or (d) polypeptides which contain at least the amino acid residues of positions 1-29;
(f) having the following specific amino acid sequences in positions 1-29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X (cyclic disulfide);
wherein the C-terminal amino acid and X are as defined above; and modification of any one of these group (f) compounds in accordance with the modifications set forth in (b), (c) and (d) above; and
(g) organic or inorganic addition salts of any of said (a), (b), (c), (d), (e) or (f) polypeptides of Group 1.

3. A composition effective to cause the release and elevation of the level of growth hormone in the blood of an animal, the composition comprising an effective amount of polypeptides selected from at least two different groups of Group 1 polypeptides, Group 2 polypeptides or Group 3 polypeptides.
wherein Group 1 polypeptides are selected from any polypeptides:
(a) having the following amino acid sequences in positions 1-44 (numbered from N terminus to C terminus):
(#144)    YADAIFTNSYRKVLGQLSARKLL-QDIMSRQQGESNQERGARARL-CONH₂ (hGHRH),
(#145)    YADAIFTNSYRKVLGQLSARKLL-QDIMSRQQGERNQEQGARVRL-CONH₂ (pGHRH),
(#146)    YADAIFTNSYRKVLGQLSARKLL-QDIMNRQQGERNQEQGAKVRL-CONH₂ (bGHRH),
(#148)    YADAIFTNSYRKILGQLSARKLL-QDIMNRQQGERNQEQGAKVRL-CONH₂ (oGHRH), and
(#149)    HADAIFTSSYRRILGQLYARKL-LHEIMNRQQGERNQEQRSRFN-COOH (rGHRH);
wherein the C-terminal amino acid has the following truncated general formula:

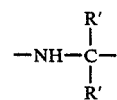

wherein each R' independently represents the substituents of the particular amino acid residue, e.g.; hydrogen, alkyl, aryl, amino or acid substituents; X denotes the C terminal end group and is selected from —CONH₂, —COOH, —COOR, —CONRR, —CH₂OH, and —CH₂OR, where R is an alkyl group having 1-6 carbon atoms or an aromatic ring having up to 12 carbon atoms; and wherein the amino acid residue abbreviations used are in accordance with the standard peptide nomenclature:
G=Gly (Glycine),
Y=Tyr (Tyrosine),
I=Ile (L-Isoleucine),
E=Glu (L-Glutamic Acid),
T=Thr (L-Threonine),
F=Phe (L-Phenylalanine),
A=Ala (L-Alanine),
K=Lys (L-Lysine),
D=Asp (L-Aspartic Acid),
C=Cys (L-Cysteine),
R=Arg (L-Arginine),
Q=Gln (L-Glutamine),
P=Pro (L-Proline),
L=Leu (L-Leucine),
M=Met (L-Methionine),
S=Ser (L-Serine),
N=Asn (L-Asparagine),
H=His (L-Histidine),
W=Trp (L-Tryptophan), and
V=Val (L-Valine);
(b) any one of said (a) polypeptides having the following amino acid substitutions:
position 1 of (#144–#148) is DTyr or His;
position 1 of (#149) is Tyr;
position 2 of (#144–#149) is (NMe)DAla or Aib or DAla;
position 3 of (#144–#149) is DAsp;
position 4 of (#144–#149) is DAla;
position 1+2 of (#144–#149) is DTyr¹+DAla²;
(c) any one of said (a) or (b) polypeptides having a substitution of Nle for Met at position 27;
(d) any one of said (a), (b), or (c) polypeptides in which the N-terminus —NH₂ is replaced by —NHCOCH₃;
(e) fragments of any one of said (a), (b), (c) or (d) polypeptides which contain at least the amino acid residues of positions 1-29,
(f) having the following amino acid sequences in positions 1-29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X (cyclic disulfide);
wherein the C-terminal amino acid and X are as defined above; and modification of any one of these group (f) compounds in accordance with the modifications set forth in (b), (c) and (d) above; and
(g) organic or inorganic addition salts of any of said (a), (b), (c), (d), (e) or (f) polypeptides of Group 1;
Group 2 polypeptides are selected from any of polypeptides having the structure:
His-DTrp-Ala-Trp-DPhe-Lys-NH₂;
DOPA-Ala-His-DTrp-Ala-Trp-DPhe-Lys-NH₂;
Phe-Ala-His-DTrp-Ala-Trp-DPhe-Lys-NH₂;
Ala-His-(formyl)DTrp-Ala-Trp-DPhe-Lys-NH₂ (DTrp is formylated at the indole nitrogen);
Ala-His-DTrp-Ser-Trp-DPhe-Lys-NH₂;
His-DTrp-Ala-Trp-DPhe-Lys-Ala-Tyr-NH₂;
Lys-Ala-His-DTrp-Ala-Trp-DPhe-Lys-NH₂;
Tyr-Ala-His-DTrp-Ala-Trp-DPhe-Lys-NH₂;
Lys-His-DTrp-Ala-Trp-DPhe-Asp-NH₂; and
Z-His-DTrp-Ala-Trp-DPhe-Lys-NH₂;
wherein Z is selected from the group consisting of all naturally occurring L-amino acids, Met(O), DOPA and Abu; and
organic or inorganic addition salts of any of said polypeptides of Group 2; and
Group 3 polypeptides are selected from any of polypeptides having the structure:
Tyr-DArg-Phe-NH₂;
Tyr-DArg(NO₂)-Phe-NH₂;
Tyr-DMet(O)-Phe-NH₂;
Tyr-DAla-Phe-Gly-NH₂;
Tyr-DArg-Phe-Gly-NH₂;
Tyr-DArg-Phe-Sar;
Tyr-DAla-Gly-Phe-NH₂;
Tyr-DAla-Gly-(NMe)Phe-Gly-ol;
Tyr-DAla-Phe-Sar-NH₂;
Tyr-DAla-Phe-Sar-NH₂;
Tyr-DArg(NO₂)-Phe-Gly-NH₂;
Tyr-DMet(O)-Phe-Gly-NH₂;
(NMe)Tyr-DArg-Phe-Sar-NH₂;
Tyr-DAla-Phe-Gly-ol;
Tyr-DAla-Phe-Gly-Tyr-NH₂;
Gly-Tyr-DArg-Phe-Gly-NH₂;
Gly-Tyr-DAla-Phe-Gly-NH₂;
Sar-Tyr-DArg-Phe-Sar-NH₂;
Tyr-DCys-Phe-Gly-DCys-NH₂ (cyclic disulfide);
Tyr-DCys-Phe-Gly-DCys-NH₂ (free dithiol)
Tyr-DCys-Gly-Phe-DCys-NH₂ (cyclic disulfide);
Tyr-DCys-Gly-Phe-DCys-NH₂ (free dithiol);
Tyr-DAla-Phe-Gly-Tyr-Pro-Ser-NH₂;
Tyr-DAla-Phe-Sar-Tyr-Pro-Ser-NH₂;
Tyr-DAla-Phe-Gly-Tyr-Hyp-Ser-NH₂;
Tyr-DAla-Phe-Sar-Tyr-Hyp-Ser-NH₂;
Tyr-DArg-Phe-Gly-Tyr-Hyp-Ser-NH₂;
Tyr-DArg-Phe-Sar-Tyr-Pro-Ser-NH₂;
Tyr-Darg-Phe-Sar-Tyr-Hyp-Ser-NH₂;
Tyr-DArg-Phe-Gly-Tyr-Pro-Ser-NH₂;
and organic or inorganic addition salts of any of said polypeptides of Group 3.

4. A composition effective to cause the release and elevation of the level of growth hormone in the blood of a mammal, the composition comprising an effective amount of polypeptides selected from at least two different groups of Group 1 polypeptides, Group 2 polypeptides or Group 3 polypeptides.
wherein Group 1 polypeptides are selected from any of the polypeptides:
(a) having the following amino acid sequences in positions 1–44 (numbered from N terminus to C terminus):
(#144) YADAIFTNSYRKVLGQLSARKLL-QDIMSRQQGESNQERGARARL-CONH₂ (hGHRH),
(#145) YADAIFTNSYRKVLGQLSARKLL-QDIMSRQQGERNQEQGARVRL-CONH₂ (pGHRH),
(#146) YADAIFTNSYRKVLGQLSARKLL-QDIMNRQQGERNQEQGAKVRL-CONH₂ (bGHRH),
(#148) YADAIFTNSYRKILGQLSARKLL-QDIMNRQQGERNQEQGAKVRL-CONH₂ (oGHRH), and (#149) HADAIFTSSYRRILGQLYARKL-LHEIMNRQQGERNQEQRSRFN-COOH (rGHRH);

wherein the C-terminal amino acid has the following truncated general formula:

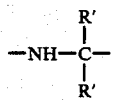

wherein each R' independently represents the substituents of the particular amino acid residue, e.g.; hydrogen, alkyl, aryl, amino or acid substituents; X denotes the C terminal end group and is selected from —CONH$_2$, —COOH, —COOR, —CONRR, —CH$_2$OH, and —CH$_2$OR, where R is an alkyl group having 1–6 carbon atoms or an aromatic ring having up to 12 carbon atoms; and wherein the amino acid residue abbreviations used are in accordance with the standard peptide nomenclature:
G=Gly (Glycine),
Y=Tyr (Tyrosine),
I=Ile (L-Isoleucine),
E=Glu (L-Glutamic Acid),
T=Thr (L-Threonine),
F=Phe (L-Phenylalanine),
A=Ala (L-Alanine),
K=Lys (L-Lysine),
D=Asp (L-Aspartic Acid),
C=Cys (L-Cysteine),
R=Arg (L-Arginine),
Q=Gln (L-Glutamine),
P=Pro (L-Proline),
L=Leu (L-Leucine),
M=Met (L-Methionine),
S=Ser (L-Serine),
N=Asn (L-Asparagine),
H=His (L-Histidine),
W=Trp (L-Tryptophan), and
V=Val (L-Valine);

(b) any one of said (a) polypeptides having a substitution of Nle for Met at position 27;
(c) any one of said (a) or (b) polypeptides in which the N-terminus —NH$_2$ is replaced by —NHCOCH$_3$;
(d) fragments of any one of said (a), (b) or (c) polypeptides which contain at least the amino acid residues of positions 1–29,
(e) having the following amino acid sequences in positions 1–29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X, (cyclic disulfide);
wherein the C-terminal amino acid and X are as defined above; and modification of any one of these group (e) compounds in accordance with the modifications set forth in (b), (c) and (d) above;
(f) organic or inorganic addition salts of any of said (a), (b), (c), (d) or (e) polypeptides of Group 1;

Group 2 polypeptides are selected from any of the polypeptides having the structure:
His-DTrp-Ala-Trp-DPhe-Lys-NH$_2$;
DOPA-Ala-His-DTrp-Ala-Trp-DPhe-Lys-NH$_2$;
His-DTrp-Ala-Trp-DPhe-Lys-Ala-Tyr-NH$_2$;
Lys-Ala-His-DTrp-Ala-Trp-DPhe-Lys-NH$_2$;
Tyr-Ala-His-DTrp-Ala-Trp-DPhe-Lys-NH$_2$;
Phe-Ala-His-DTrp-Ala-Trp-DPhe-Lys-NH$_2$;
Z-His-DTrp-Ala-Trp-DPhe-Lys-NH$_2$;
wherein Z is selected from the group consisting of Ala, Val, DOPA, Trp, Met, Lys, Asp, Met(O), Leu, Abu and Arg, and
organic or inorganic addition salts of any of said polypeptides of Group 2; and
Group 3 polypeptides are selected from any of the polypeptides having the structure:
Tyr-DArg-Phe-NH$_2$;
Tyr-DAla-Phe-Gly-NH$_2$;
Tyr-DArg-Phe-Gly-NH$_2$;
Tyr-DArg-Phe-Sar;
Tyr-DAla-Gly-Phe-NH$_2$;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Phe-Gly-ol;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Gly-Tyr-DArg-Phe-Gly-NH$_2$;
Tyr-DAla-Phe-Sar-Tyr-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DAla-Phe-Gly-Tyr-Pro-Ser-NH$_2$;
Tyr-DArg-Phe-Gly-Tyr-Pro-Ser-NH$_2$;
Tyr-DArg-Phe-Gly-Tyr-Hyp-Ser-NH$_2$;
and organic or inorganic addition salts of any of said polypeptides of Group 3.

5. Composition of claim 1 comprising a compound from each of Group 1 polypeptides and Group 2 polypeptides.

6. Composition of claim 1 comprising a compound from each of Group 1 polypeptides and Group 3 polypeptides.

7. Composition of claim 1 comprising a compound from each of Group 2 polypeptides and Group 3 polypeptides.

8. Composition of claim 1 comprising a compound from each of Group 1 polypeptides, Group 2 polypeptides and Group 3 polypeptides.

9. Composition of claim 3 comprising a compound from each of Group 1 polypeptides and Group 2 polypeptides.

10. Composition of claim 3 comprising a compound from each of Group 1 polypeptides and Group 3 polypeptides.

11. Composition of claim 3 comprising a compound from each of Group 2 polypeptides and Group 3 polypeptides.

12. Composition of claim 3 comprising a compound from each of Group 1 polypeptides, Group 2 polypeptides and Group 3 polypeptides.

13. Composition of claim 4 comprising a compound from each of Group 1 polypeptides and Group 2 polypeptides.

14. Composition of claim 4 comprising a compound from each of Group 1 polypeptides and Group 3 polypeptides.

15. Composition of claim 4 comprising a compound from each of Group 2 polypeptides and Group 3 polypeptides.

16. Composition of claim 4 comprising a compound from each of Group 1 polypeptides, Group 2 polypeptides and Group 3 polypeptides.

17. Method of causing release and elevation of the level of growth hormone in the blood of an animal, comprising administering an effective dose of a combination comprising polypeptides selected from at least two different groups of Group 1 polypeptides in a ratio such that such combination is effective to cause the synergistic release and elevation of growth hormone in the blood of such animal; Group 2 polypeptides or Group 3 polypeptides.

wherein Group 1 polypeptides are selected from any of the naturally occurring growth hormone releasing hormones and functional equivalents thereof, wherein said polypeptides act at the growth hormone releasing hormone receptor of mammals and other vertebrates, and crustaceans;

Group 2 polypeptides are selected from any of the polypeptides having the structure:
Ala-His-DTrp-Ala-Trp-DPhe-Lys-Gly-Tyr-NH$_2$;
Ala-His-(formyl)DTrp-Ala-Trp-DPhe-Lys-NH$_2$ (DTrp is formylated at the indole nitrogen);
Ala-His-DTrp-Ser-Trp-DPhe-Lys-NH$_2$;
Cys-Ala-His-DTrp-Ala-Trp-DPhe-Lys-Cys-NH$_2$ (cyclic disulfide);
Cys-Ala-His-DTrp-Ala-Trp-DPhe-Lys-Cys-NH$_2$ (free dithiol);
DOPA-Ala-His-DTrp-Ala-Trp-DPhe-Lys-NH$_2$;
His-DTrp-Ala-Trp-DPhe-Lys-NH$_2$;
His-DTrp-Ala-Trp-DPhe-Lys-Ala-Tyr-NH$_2$;
Lys-Ala-His-DTrp-Ala-Trp-DPhe-Lys-NH$_2$;
Lys-His-DTrp-Ala-Trp-DPhe-Asp-NH$_2$;
Phe-Ala-His-DTrp-Ala-Trp-DPhe-Lys-NH$_2$;
Tyr-Ala-Gly-Thr-Ala-His-DTrp-Ala-Trp-DPhe-Lys-NH$_2$;
Tyr-Ala-His-DTrp-Ala-Trp-DPhe-Lys-NH$_2$;
Tyr-DAla-Phe-Gly-Ala-His-DTrp-Ala-Trp-DPhe-Lys-NH$_2$;
Tyr-DAla-Gly-Phe-Ala-His-DTrp-Ala-Trp-DPhe-Lys-NH$_2$;
Ala-His-XTrp*-Ala-Trp-DPhe-Lys-NH$_2$ (*XTrp is selected from the group consisting of all N-monomethylated Trp isomers, i.e., (N$^\alpha$Me)Trp, (N$^\alpha$Me)DTrp, (indole NMe)Trp and (indole NMe)DTrp);
Z-His-DTrp-Ala-Trp-DPhe-Lys-NH$_2$;
wherein Z is selected from the group consisting of all naturally occurring L-amino acids, Met(O), DOPA and Abu;
and organic or inorganic addition salts of any of said polypeptides of Group 2; and
Group 3 polypeptides are selected from any of the polypeptides having the structure:
Tyr-DArg-Phe-NH$_2$;
Tyr-DAla-Phe-NH$_2$;
Tyr-DArg(NO$_2$)-Phe-NH$_2$;
Tyr-DMet(O)-Phe-NH$_2$;
Tyr-DAla-Phe-Gly-NH$_2$;
Tyr-DArg-Phe-Gly-NH$_2$;
Tyr-DThr-Phe-Gly-NH$_2$;
Phe-DArg-Phe-Gly-NH$_2$;
Tyr-DArg-Phe-Sar;
Tyr-DAla-Gly-Phe-NH$_2$;
Tyr-DArg-Gly-Trp-NH$_2$;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Tyr-DArg-Phe-Gly-ol;
Tyr-DArg-Gly-(NMe)Phe-NH$_2$;
Try-DArg-Phe-Sar-ol
Try-DAla-Phe-Sar-ol
Tyr-DAla-Phe-Gly-Tyr-NH$_2$;
Gly-Tyr-DArg-Phe-Gly-NH$_2$;
Tyr-DThr-Gly-Phe-Thz-NH$_2$;
Gly-Tyr-DAla-Phe-Gly-NH$_2$;
Tyr-DAla-Phe-Gly-ol;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Phe-Sar;
Tyr-DAla-Gly-(NMe)Phe-NH$_2$;
Sar-Tyr-DArg-Phe-Sar-NH$_2$;
Tyr-DCys-Phe-Gly-DCys-NH$_2$ (cyclic disulfide);
Tyr-DCys-Phe-Gly-DCys-NH$_2$ (free dithiol);
Tyr-DCys-Gly-Phe-DCys-NH$_2$ (cyclic disulfide);
Tyr-DCys-Gly-Phe-DCys-NH$_2$ (free dithiol);
Tyr-DAla-Phe-Gly-Tyr-Pro-Ser-NH$_2$;
Tyr-DAla-Phe-Sar-Tyr-Pro-Ser-NH$_2$;
Tyr-DAla-Phe-Sar-Phe-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DAla-Phe-Sar-Phe-Hyp-Ser-NH$_2$;
Tyr-DArg-Phe-Gly-Tyr-Hyp-Ser-NH$_2$;
Tyr-DArg-Phe-Sar-Tyr-Pro-Ser-NH$_2$;
Tyr-DArg-Phe-Sar-Tyr-Hyp-Ser-NH$_2$;
Tyr-DArg-Phe-Gly-Tyr-Pro-Ser-NH$_2$; and organic or inorganic addition salts of any of said polypeptides of Group 3.

18. Method of claim 17 wherein said Group 1 polypeptides are selected from any of the polypeptides:
(a) having the following amino acid sequences in positions 1–44 (numbered from N terminus to C terminus):
(#144)   YADAIFTNSYRKVLGQLSARKLL-QDIMSRQQGESNQERGARARL-X,
(#145)   YADAIFTNSYRKVLGQLSARKLL-QDIMSRQQGERNQEQGARVRL-X,
(#146)   YADAIFTNSYRKVLGQLSARKLL-QDIMNRQQGERNQEQGAKVRL-X,
(#148)   YADAIFTNSYRKILGQLSARKLL-QDIMNRQQGERNQEQGAKVRL-X,
(#149)   HADAIFTSSYRRILGQLYARKL-LHEIMNRQQGERNQEQRSRFN-X; and functional equivalents thereof;
wherein the C-terminal amino acid has the following truncated general formula:

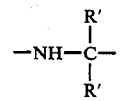

wherein each R' independently represents the substituents of the particular amino acid residue, e.g.; hydrogen, alkyl, aryl, amino or acid substituents; X denotes the C terminal end group and is selected from —CONH$_2$, —COOH, —COOR, —CONRR, —CH$_2$OH, and —CH$_2$OR, where R is an alkyl group having 1–6 carbon atoms or an aromatic ring having up to 12 carbon atoms; and wherein the amino acid residue abbreviations used are in accordance with the standard peptide nomenclature:
G=Gly (Glycine),
Y=Tyr (L-Tyrosine),
I=Ile (L-Isoleucine),
E=Glu (L-Glutamic Acid),
T=Thr (L-Threonine),
F=Phe (L-Phenylalanine),
A=Ala (L-Alanine),
K=Lys (L-Lysine),
D=Asp (L-Aspartic Acid),
C=Cys (L-Cysteine),
R=Arg (L-Arginine),
Q=Gln (L-Glutamine),
P=Pro (L-Proline),
L=Leu (L-Leucine),
M=Met (L-Methionine),
S=Ser (L-Serine),
N=Asn (L-Asparagine),
H=His (L-Histidine),
W=Trp (L-Tryptophan), and
V=Val (L-Valine);
(b) any one of said (a) polypeptides having the following amino acid substitutions:
position 1 of (#144–#148) is DTyr or His;
position 1 of (#149) is Tyr or DHis;
position 2 of (#144–#149) is (NMe)DAla or Aib or DAla;
position 3 of (#144–#149) is DAsp;
position 4 of (#144–#149) is DAla; and
position 1+2 of (#144–#149) is;
  $DTyr^1+DAla^2$, $DTyr^1+(NMe)DAla^2$, or $DTyr^1+Aib^2$;
(c) any one of said (a) or (b) polypeptides having a substitution of Nle for Met at position 27;
(d) any one of said (a), (b) or (c) polypeptides in which the N-terminus —NH$_2$ is replaced by —NHCOR and wherein R is an alkyl group having 1 to 6 carbon atoms, or an aromatic ring having up to 12 carbon atoms;
(e) fragments of any one of said (a), (b), (c) or (d) polypeptides which contain at least the amino acid residues of positions 1–29;
(f) having the following specific amino acid sequences in positions 1–29 (numbered from N terminus to C terminus);
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X (cyclic disulfide);
wherein the C-terminal amino acid and X are as defined above; and modification of any one of these group (f) compounds in accordance with the modifications set forth in (b), (c) and (d) above; and
(g) organic or inorganic addition salts of any of said (a), (b), (c), (d), (e) or (f) polypeptides of Group 1.

19. Method of causing release and elevation of the level of growth hormone in the blood of an animal, comprising administering an effective dose of a combination comprising polypeptides selected from at least two different groups of Group 1 polypeptides, Group 2 polypeptides or Group 3 polypeptides, in a ratio such that such composition is effective to cause the synergistic release and elevation of growth hormone in the blood of such animal; wherein Group 1 polypeptides are selected from any polypeptides:
(a) having the following amino acid sequences in positions 1–44 (numbered from N terminus to C terminus):
(#144) YADAIFTNSYRKVLGQLSARKLL-QDIMSRQQGESNQERGARARL-CONH$_2$ (hGHRH),
(#145) YADAIFTNSYRKVLGQLSARKLL-QDIMSRQQGERNQEQGARVRL-CONH$_2$ (pGHRH),
(#146) YADAIFTNSYRKVLGQLSARKLL-QDIMNRQQGERNQEQGAKVRL-CONH$_2$ (bGHRH),
(#148) YADAIFTNSYRKILGQLSARKLL-QDIMNRQQGERNQEQGAKVRL-CONH$_2$ (oGHRH), and
(#149) HADAIFTSSYRRILGQLYARKL-LHEIMNRQQGERNQEQRSRFN-COOH (rGHRH);
wherein the C-terminal amino acid has the following truncated general formula:

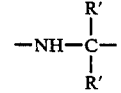

wherein each R' independently represents the substituents of the particular amino acid residue, e.g.; hydrogen, alkyl, aryl, amino or acid substituents; X denotes the C terminal end group and is selected from —CONH$_2$, —COOH, —COOR, —CONRR, —CH$_2$OH, and —CH$_2$OR, where R is an alkyl group having 1–6 carbon atoms or an aromatic ring having up to 12 carbon atoms; and wherein the amino acid residue abbreviations used are in accordance with the standard peptide nomenclature:
G=Gly (Glycine),
Y=Tyr (Tyrosine),
I=Ile (L-Isoleucine),
E=Glu (L-Glutamic Acid),
T=Thr (L-Threonine),
F=Phe (L-Phenylalanine),
A=Ala (L-Alanine),
K=Lys (L-Lysine),
D=Asp (L-Aspartic Acid),
C=Cys (L-Cysteine),
R=Arg (L-Arginine),
Q=Gln (L-Glutamine),
P=Pro (L-Proline),
L=Leu (L-Leucine),
M=Met (L-Methionine),
S=Ser (L-Serine),
N=Asn (L-Asparagine),
H=His (L-Histidine),
W=Trp (L-Tryptophan), and
V=Val (L-Valine);
(b) any one of said (a) polypeptides having the following amino acid substitutions:
position 1 of (#144–#148) is DTyr or His;
position 1 of (#149) is Tyr;
position 2 of (#144–#149) is (NMe)DAla or Aib or DAla;
position 3 of (#144–#149) is DAsp;
position 4 of (#144–#149) is DAla;

position 1+2 of (#144–#149) is DTyr¹+DAla²;
(c) any one of said (a) or (b) polypeptides having a substitution of Nle for Met at position 27;
(d) any one of said (a), (b), or (c) polypeptides in which the N-terminus —NH₂ is replaced by —NHCOCH₃;
(e) fragments of any one of said (a), (b), (c) or (d) polypeptides which contain at least the amino acid residues of positions 1–29,
(f) having the following amino acid sequences in positions 1–29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X (cyclic disulfide);
wherein the C-terminal amino acid and X are as defined above; and modification of any one of these group (f) compounds in accordance with the modifications set forth in (b), (c) and (d) above; and
(g) organic or inorganic addition salts of any of said (a), (b), (c), (d), (e) or (f) polypeptides of Group 1;
Group 2 polypeptides are selected from any of polypeptides having the structure:
His-DTrp-Ala-Trp-DPhe-Lys-NH₂;
DOPA-Ala-His-DTrp-Ala-Trp-DPhe-Lys-NH₂;
Phe-Ala-His-DTrp-Ala-Trp-DPhe-Lys-NH₂;
Ala-His-(formyl)DTrp-Ala-Trp-DPhe-Lys-NH₂ (DTrp is formylated at the indole nitrogen);
Ala-His-DTrp-Ser-Trp-DPhe-Lys-NH₂;
His-DTrp-Ala-Trp-DPhe-Lys-Ala-Tyr-NH₂;
Lys-Ala-His-DTrp-Ala-Trp-DPhe-Lys-NH₂;
Tyr-Ala-His-DTrp-Ala-Trp-DPhe-Lys-NH₂;
Lys-His-DTrp-Ala-Trp-DPhe-Asp-NH₂; and
Z-His-DTrp-Ala-Trp-DPhe-Lys-NH₂;
wherein Z is selected from the group consisting of all naturally occurring L-amino acids, Met(O), DOPA and Abu; and
organic or inorganic addition salts of any of said polypeptides of Group 2; and
Group 3 polypeptides are selected from any of polypeptides having the structure:
Tyr-DArg-Phe-NH₂;
Tyr-DArg(NO₂)-Phe-NH₂;
Tyr-DMet(O)-Phe-NH₂;
Tyr-DAla-Phe-Gly-NH₂;
Tyr-DArg-Phe-Gly-NH₂;
Tyr-DArg-Phe-Sar;
Tyr-DAla-Gly-Phe-NH₂;
Tyr-DAla-Gly-(NMe)Phe-Gly-ol;
Tyr-DAla-Phe-Sar-NH₂;
Tyr-DAla-Phe-Sar-NH₂;
Tyr-DArg(NO₂)-Phe-Gly-NH₂;
Tyr-DMet(O)-Phe-Gly-NH₂;
(NMe)Tyr-DArg-Phe-Sar-NH₂;
Tyr-DAla-Phe-Gly-ol;
Tyr-DAla-Phe-Gly-Tyr-NH₂;
Gly-Tyr-DArg-Phe-Gly-NH₂;
Gly-Tyr-DAla-Phe-Gly-NH₂;
Sar-Tyr-DArg-Phe-Sar-NH₂;
Tyr-DCys-Phe-Gly-DCys-NH₂ (cyclic disulfide);
Tyr-DCys-Phe-Gly-DCys-NH₂ (free dithiol)
Tyr-DCys-Gly-Phe-DCys-NH₂ (cyclic disulfide);
Tyr-DCys-Gly-Phe-DCys-NH₂ (free dithiol);
Tyr-DAla-Phe-Gly-Tyr-Pro-Ser-NH₂;
Tyr-DAla-Phe-Sar-Tyr-Pro-Ser-NH₂;
Tyr-DAla-Phe-Gly-Tyr-Hyp-Ser-NH₂;
Tyr-DAla-Phe-Sar-Tyr-Hyp-Ser-NH₂;
Tyr-DArg-Phe-Gly-Tyr-Hyp-Ser-NH₂;
Tyr-DArg-Phe-Sar-Tyr-Pro-Ser-NH₂;
Tyr-Darg-Phe-Sar-Tyr-Hyp-Ser-NH₂;
Tyr-DArg-Phe-Gly-Tyr-Pro-Ser-NH₂;
and organic or inorganic addition salts of any of said polypeptides of Group 3.

20. Method of causing release and elevation of the level of growth hormone in the blood of a mammal, comprising administering an effective dose of a combination comprising polypeptides selected from at least two different groups of Group 1 polypeptides, Group 2 polypeptides or Group 3 polypeptides in a ratio such that such combination is effective to cause the synergistic release and elevation of growth hormone in the blood of such mammal; wherein Group 1 polypeptides are selected from any of the polypeptides:
(a) having the following amino acid sequences in positions 1–44 (numbered from N terminus to C terminus):
(#144) YADAIFTNSYRKVLGQLSARKLL-QDIMSRQQGESNQERGARARL-CONH₂ (hGHRH),
(#145) YADAIFTNSYRKVLGQLSARKLL-QDIMSRQQGERNQEQGARVRL-CONH₂ (pGHRH),
(#146) YADAIFTNSYRKVLGQLSARKLL-QDIMNRQQGERNQEQGAKVRL-CONH₂ (bGHRH),
(#148) YADAIFTNSYRKILGQLSARKLL-QDIMNRQQGERNQEQGAKVRL-CONH₂ (oGHRH), and
(#149) HADAIFTSSYRRILGQLYARKL-LHEIMNRQQGERNQEQRSRFN-COOH (rGHRH);
wherein the C-terminal amino acid has the following truncated general formula:

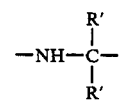

wherein each R' independently represents the substituents of the particular amino acid residue, e.g.; hydrogen, alkyl, aryl, amino or acid substituents; X denotes the C terminal end group and is selected from —CONH₂, —COOH, —COOR, —CONRR, —CH₂OH, and —CH₂OR, where R is an alkyl group having 1–6 carbon atoms or an aromatic ring having up to 12 carbon atoms; and wherein the amino acid residue abbreviations used are in accordance with the standard peptide nomenclature:
G=Gly (Glycine),
Y=Tyr (L-Tyrosine),
I=Ile (L-Isoleucine),
E=Glu (L-Glutamic Acid),
T=Thr (L-Threonine),
F=Phe (L-Phenylalanine),
A=Ala (L-Alanine),
K=Lys (L-Lysine),
D=Asp (L-Aspartic Acid),
C=Cys (L-Cysteine),
R=Arg (L-Arginine), Q=Gln (L-Glutamine),
P=Pro (L-Proline),
L=Leu (L-Leucine),
M=Met (L-Methionine),
S=Ser (L-Serine),
N=Asn (L-Asparagine),
H=His (L-Histidine),
W=Trp (L-Tryptophan), and
V=Val (L-Valine);

(b) any one of said (a) polypeptides having a substitution of Nle for Met at position 27;

(c) any one of said (a) or (b) polypeptides in which the N-terminus —NH$_2$ is replaced by —NHCOCH$_3$;

(d) fragments of any one of said (a), (b) or (c) polypeptides which contain at least the amino acid residues of positions 1–29, (e) having the following amino acid sequences in positions 1–29 (numbered from N terminus to C terminus):
YADAIFTNSYRKVLQQLAARKLLQDIMSR-X,
YADAIFTNSYRKVLQQLLARKLLQDIMSR-X,
YSDAIFSNAYRKILQQLLARKLLQDIMQR-X,
YADAIFSNAYRKILQQLLARKLLQDIMQR-X,
YADAIFSSAYRRLLAQLASRRLLQELLAR-X,
YADAIFTNCYRKVLCQLSARKLLQDIMSR-X (linear dithiol), and
YADAIFTNCYRKVLCQLSARKLLQDIMSR-X, (cyclic disulfide);
wherein the C-terminal amino acid and X are as defined above; and modification of any one of these group (e) compounds in accordance with the modifications set forth in (b), (c) and (d) above;

(f) organic or inorganic addition salts of any of said (a), (b), (c), (d) or (e) polypeptides of Group 1;

Group 2 polypeptides are selected from any of the polypeptides having the structure:
His-DTrp-Ala-Trp-DPhe-Lys-NH$_2$;
DOPA-Ala-His-DTrp-Ala-Trp-DPhe-Lys-NH$_2$;
His-DTrp-Ala-Trp-DPhe-Lys-Ala-Tyr-NH$_2$;
Lys-Ala-His-DTrp-Ala-Trp-DPhe-Lys-NH$_2$;
Tyr-Ala-His-DTrp-Ala-Trp-DPhe-Lys-NH$_2$;
Phe-Ala-His-DTrp-Ala-TRp-DPhe-Lys-NH$_2$;
Z-His-DTrp-Ala-Trp-DPhe-Lys-NH$_2$;
wherein Z is selected from the group consisting of Ala, Val, DOPA, Trp, Met, Lys, Asp, Met(O), Leu, Abu and Arg, and
organic or inorganic addition salts of any of said polypeptides of Group 2; and
Group 3 polypeptides are selected from any of the polypeptides having the structure:
Tyr-DArg-Phe-NH$_2$;
Tyr-DAla-Phe-Gly-NH$_2$;
Tyr-DArg-Phe-Gly-NH$_2$;
Tyr-DArg-Phe-Sar;
Tyr-DAla-Gly-Phe-NH$_2$;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Phe-Gly-ol;
Tyr-DArg(NO$_2$)-Phe-Gly-NH$_2$;
Tyr-DMet(O)-Phe-Gly-NH$_2$;
(NMe)Tyr-DArg-Phe-Sar-NH$_2$;
Gly-Tyr-DArg-Phe-Gly-NH$_2$;
Tyr-DAla-Phe-Sar-Tyr-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DAla-Phe-Gly-Tyr-Pro-Ser-NH$_2$;
Tyr-DArg-Phe-Gly-Tyr-Pro-Ser-NH$_2$;
Tyr-DArg-Phe-Gly-Tyr-Hyp-Ser-NH$_2$;
and organic or inorganic addition salts of any of said polypeptides of Group 3.

21. Method of claim 17 wherein said combination comprises a compound from each of Group 1 polypeptides and Group 2 polypeptides.

22. Method of claim 17 wherein said combination comprises a compound from each of Group 1 polypeptides and Group 3 polypeptides.

23. Method of claim 17 wherein said combination comprises a compound from each of Group 2 polypeptides and Group 3 polypeptides.

24. Method of claim 17 wherein said combination comprises a compound from each of Group 1 polypeptides, Group 2 polypeptides and Group 3 polypeptides.

25. Method of claim 19 wherein said combination comprises a compound from each of Group 1 polypeptides and Group 2 polypeptides.

26. Method of claim 19 wherein said combination comprises a compound from each of Group 1 polypeptides and Group 3 polypeptides.

27. Method of claim 19 wherein said combination comprises a compound from each of Group 2 polypeptides and Group 3 polypeptides.

28. Method of claim 19 wherein said combination comprises a compound from each of Group 1 polypeptides, Group 2 polypeptides and Group 3 polypeptides.

29. Method of claim 20 wherein said combination comprises a compound from each of Group 1 polypeptides and Group 2 polypeptides.

30. Method of claim 20 wherein said combination comprises a compound from each of Group 1 polypeptides and Group 3 polypeptides.

31. Method of claim 20 wherein said combination comprises a compound from each of Group 2 polypeptides and Group 3 polypeptides.

32. Method of claim 20 wherein said combination comprises a compound from each of Group 1 polypeptides, Group 2 polypeptides and Group 3 polypeptides.

* * * * *